United States Patent
Soin

(10) Patent No.: US 11,065,450 B1
(45) Date of Patent: Jul. 20, 2021

(54) NEUROMODULATION SYSTEM AND METHOD WITH FEEDBACK OPTIMIZED ELECTRICAL FIELD GENERATION

(71) Applicant: Soin Neuroscience, LLC, Dayton, OH (US)

(72) Inventor: Amol N. Soin, Dayton, OH (US)

(73) Assignee: Soin Neuroscience, LLC, Dayton, OH (US)

( * ) Notice: Subject to any disclaimer, the term of this patent is extended or adjusted under 35 U.S.C. 154(b) by 0 days.

(21) Appl. No.: 17/111,950

(22) Filed: Dec. 4, 2020

Related U.S. Application Data

(63) Continuation of application No. 17/109,512, filed on Dec. 2, 2020, now Pat. No. 10,953,231, which is a continuation of application No. 16/848,691, filed on Apr. 14, 2020, now Pat. No. 10,857,364.

(51) Int. Cl.
*A61N 1/36* (2006.01)

(52) U.S. Cl.
CPC ....... *A61N 1/36142* (2013.01); *A61N 1/3614* (2017.08); *A61N 1/3616* (2013.01); *A61N 1/36067* (2013.01); *A61N 1/36071* (2013.01); *A61N 1/36082* (2013.01); *A61N 1/36192* (2013.01)

(58) Field of Classification Search
CPC ............ A61N 1/36142; A61N 1/36071; A61N 1/36192; A61N 1/3616; A61N 1/36082; A61N 1/3614; A61N 1/36067
USPC .......................................................... 607/46
See application file for complete search history.

(56) References Cited

U.S. PATENT DOCUMENTS

| | | |
|---|---|---|
| 5,327,902 A | 7/1994 | Lemmen |
| 8,774,934 B2 | 7/2014 | Doerr |
| 8,812,115 B2 | 8/2014 | Lee |
| 9,737,703 B2 | 8/2017 | Carbunaru |
| 10,342,606 B2 | 7/2019 | Cosman |
| 10,352,776 B2 | 7/2019 | Feldman |

(Continued)

FOREIGN PATENT DOCUMENTS

| | | | |
|---|---|---|---|
| AU | 2008324795 B2 | 6/2014 | |
| WO | WO 2018/136354 A1 * | 1/2018 | ............... A61N 1/36 |
| WO | 2018136354 A1 | 7/2018 | |

OTHER PUBLICATIONS

PCT Search Report and Opinion for PCT/US20/63502; dated Feb. 25, 2021.

*Primary Examiner* — Amanda K Hulbert
*Assistant Examiner* — Philip C Edwards
(74) *Attorney, Agent, or Firm* — Neustel Law Offices

(57) ABSTRACT

A neuromodulation system and method with feedback optimized electrical field generation for stimulating target tissue of a patient to treat neurological and non-neurological conditions. The system generally includes implantable electrodes, implantable sensors, an implantable or external electrical signal generator, and an implantable or external controller. The controller controls the electrical signal generator to generate electrical noise stimulation signals that are delivered to the target tissue via the electrodes and that produce an optimized electric field having maximized voltage with low current density. The sensors produce temperature and impedance data for the target tissue and the controller automatically responds to values of the sensor data that indicate potential damage to the target tissue to reduce the strength of the electric field.

30 Claims, 15 Drawing Sheets

(56) References Cited

U.S. PATENT DOCUMENTS

| | | |
|---|---|---|
| 10,857,364 B1 | 12/2020 | Soin |
| 2007/0027486 A1 | 2/2007 | Armstrong |
| 2015/0157864 A1 | 6/2015 | Rosenberg |
| 2015/0297282 A1 | 10/2015 | Cadouri |
| 2016/0367812 A1 | 12/2016 | De Ridder |
| 2017/0001016 A1 | 1/2017 | De Ridder |
| 2017/0128725 A1* | 5/2017 | Kim .................. A61N 1/36021 |
| 2018/0200506 A1 | 7/2018 | Fang |
| 2019/0255332 A1* | 8/2019 | Trier ................. A61N 1/36139 |
| 2019/0366097 A1 | 12/2019 | Schepis |

* cited by examiner

NEUROMODULATION SYSTEM AND METHOD WITH FEEDBACK OPTIMIZED ELECTRICAL FIELD GENERATION

CROSS REFERENCE TO RELATED APPLICATIONS

The present application is a continuation of U.S. application Ser. No. 17/109,512 filed on Dec. 2, 2020, which is a continuation of U.S. application Ser. No. 16/848,691 filed on Apr. 14, 2020 which issues on Dec. 8, 2020 as U.S. Pat. No. 10,857,364. Each of the aforementioned patent applications, and any applications related thereto, is herein incorporated by reference in their entirety.

STATEMENT REGARDING FEDERALLY SPONSORED RESEARCH OR DEVELOPMENT

Not applicable to this application.

BACKGROUND

Field

Example embodiments in general relate to a neuromodulation system and method with feedback optimized electrical field generation for modulating the activity of or stimulating neural tissue, non-neural tissue, or a combination thereof as a therapeutic treatment for pain and other neurological and non-neurological conditions.

Related Art

Any discussion of the related art throughout the specification should in no way be considered as an admission that such related art is widely known or forms part of common general knowledge in the field.

A number of technologies and methods have been used to treat neurological and non-neurological conditions such as pain, incontinence, depression, obesity, headaches, and others. Both destructive and non-destructive methods have been used to treat pain. Various destructive methods have been used to treat chronic pain indications including radiofrequency (RF) ablation, cryoablation, chemical ablation (phenols, Botox®), ultrasonography ablation and mechanical transection. However, destructive methods cause destruction of the portion of a nerve in the treatment zone, which in turn causes an immediate loss of functionality (e.g., motor, sensory, and proprioception) and may lead to long-term atrophy, neuropathy and more pain. Consequently, destructive methods are typically treatments of last resort, and should be used sparingly.

Various non-destructive methods also have been used to treat pain including the use of prescription pain medications (opioids), local anesthetic injections, topical cocktails consisting of steroids and other anti-inflammatory agents, continuous infusion of local anesthetics, and electrical stimulation. Each method presents a unique set of challenges that can compromise treatment efficacy and/or usability.

For example, non-destructive methods using drugs, typically including opioids, can put patients at risk for unwanted side effects such as constipation, nausea, emesis, and ileus, and can ultimately result in addiction and even death. Non-destructive methods using injections of local anesthetic and/or cocktails typically have a short effective duration which may last only a period of hours, and may become ineffective over time. Such methods thus typically require continued, daily maintenance. Continuous infusion of anesthetics generally requires an external device be tethered to the patient for long-term treatment, often over a period of days. Daily device maintenance is thus a burden for patients and is often an unwanted reminder that they have pain. The use of local anesthetics and long-lasting locals (e.g., Exparel®) may also cause nerve toxicity, vascular toxicity and allergic reactions. Further, these agents are not immediately reversible, titratable or selective to the type of nerve activity that they block (e.g., pain vs. motor).

Electrical stimulation technologies have been used to mitigate both acute (e.g., post-surgical) and chronic pain types. Unlike pharmaceutical interventions, electrical stimulation technologies are reversible, non-addictive, and can be selective depending on their stimulation paradigm and treatment site. Electrical stimulation can be delivered to various parts of the central and peripheral nervous systems, including the sensory receptors in the brain, spinal cord, skin, and various peripheral nerves. Moreover, electrical stimulators can be configured to provide treatment in a transcutaneous, percutaneous, and/or implantable fashion.

Two electrical stimulation paradigms have been primarily used for the treatment of pain, both employing electrical signals with periodic waveforms. Traditional stimulation uses relatively low frequency (e.g., <1500 Hz) electrical signals to produce paresthesia, which can to some extent mask pain with a sensation of tingling or numbness. Sub-sensory paresthesia stimulation, such as employed in the HF10® technology by Nevro Corp., uses relatively higher frequency (e.g, 10 KHz range) electrical signals to at least partially block the transmission of nerve signals to the brain. See, e.g., International Patent App. Pub. No. WO 2009/061813 A1.

Unlike local anesthetics, neither of these electrical stimulation types completely eliminates painful sensations. Traditional stimulation only attenuates painful sensations, and simultaneously elicits electrical paresthesia (i.e., a buzzing, tingling, or vibration sensation), which covers the receptive field of the stimulated nerve. Sub-sensory paresthesia stimulation does not elicit electrical paresthesia but is still effective at attenuating painful sensations. Further, despite the promise of electrical stimulation, its therapeutic efficacy can reduce after a few years of use. This phenomenon is known as neurological tolerance and is the major reason for the removal of implanted stimulators from patients. Still further, the use of periodic electrical stimulation signals with relatively low frequency, e.g., less than about 100 KHz, deliver relatively short-term therapeutic effects. Thus, while the therapeutic effects from electrical stimulation using such signals typically begin to be felt within minutes-to-hours after the stimulation begins, they tend to only last for a relatively short period of time, e.g., a few hours, after the therapy has been discontinued. Because the therapeutic effects tend to be short-lived, continuous and/or frequent stimulation sessions are generally required to provide therapeutic effects that are felt for longer periods of time. This, in turn, typically results in the need for on-going device maintenance (e.g., daily battery charging) which is burdensome and inconvenient.

Electrical stimulation has also been used to treat other neurological and non-neurological conditions such as incontinence, obesity and others. For example, electrical stimulation signals have been applied to the nerves, e.g., sacral and posterior tibial nerves, and muscles, e.g., pelvic muscles, associated with the bladder and with urination as a treatment for incontinence. Electrical stimulation of the intestinal tract has been used as a treatment for gastrointestinal motility disorders and obesity. Electrical stimulation signals also have been applied to the nerves and muscles of the stomach in order to inhibit or mitigate the sensation of hunger and/or to modulate gastric motor function as a treatment for obesity and to help control chronic nausea and vomiting associated with gastroparesis as a result of diabetes.

Recently, International Patent App. Pub No. WO 2018/136354 A1 ("the '354 Application") has disclosed to employ electrical signals exhibiting statistically random waveforms, i.e., noise, to provide stimulation or modulation of neural tissue, non-neural tissue, or a combination thereof to treat pain and certain other neurological disorders. According to the '354 Application the electrical noise signals can be tuned and can thus provide better patient outcomes than conventional periodic electrical signals. The '354 Application discloses to tune or adjust the electrical noise signals by delivering the noise signals to a patient and then tuning or adjusting the signals based on feedback provided by the patient as to what the patient is feeling. However, if the patient is unable to provide accurate and timely feedback, the noise signals cannot be accurately or properly tuned, and the resulting effects will be therapeutically sub-optimal and possibly even adverse. The patient could even suffer discomfort or tissue damage as a result.

The use of tunable statistically random electrical noise signals to modulate or stimulate neural tissue, non-neural tissue or a combination of both as described in the '354 Application can provide improved therapeutic results compared to the use of conventional periodic electrical signals. However, the present inventor has discovered that even better and longer-lasting therapeutic results can be achieved by optimizing and maximizing the electric field produced in the target tissue. Optimizing and maximizing the electric field in the target tissue produces long-term plastic functional change in the tissue. As a result, relatively shorter and less frequent treatments can provide therapeutic results that remain effective over relatively long periods of time without the need to apply electrical signals to the target tissue continuously or repeatedly at short intervals. At the same time, the electric field must be optimized and maximized in a way that does not cause the patient discomfort or subject the target tissue to potential damage. Further, the optimized and maximized electric field must be rapidly and automatically controlled in response to changes in physical parameters associated with the target tissue to avoid causing patient discomfort or tissue damage.

There is thus a need for a neuromodulation system and method that addresses various deficiencies and drawbacks of conventional treatment apparatuses and methods. More specifically, there is a need for such a system and method that uses electrical noise signals to modulate or stimulate target neural tissue, non-neural tissue, or a combination thereof to effectively treat neurological and non-neurological conditions including but not limited to acute and chronic pain types, Parkinson's disease, seizures, depression, bowl/bladder incontinence, obesity (to induce less appetite), etc. There is a need for such a system and method that is non-destructive to the tissue treated, that preserves all other neurological functions of the tissue such as touch, motors, proprioception, etc., and that provides effective therapeutic results without inducing tolerance. There is a need for such a system and method that can apply less frequent and shorter treatments and produce therapeutic results that are effective over relatively long periods of time, thus also reducing the need for device maintenance, e.g., battery re-charging. There is a need for such a system and method that can optimize and maximize the electrical field produced in the target tissue to achieve the foregoing therapeutic effects while rapidly and automatically controlling the electric field in response to changes in physical parameters associated with the tissue to avoid causing patient discomfort or tissue damage.

SUMMARY

Example embodiments are directed to a neuromodulation system and method with feedback optimized electrical field generation to provide a therapeutic effect to target tissue of a patient. The target tissue can be neurological tissue, non-neurological tissue, or a combination of both. The target tissue can be tissue that is within or adjacent to tissue of the patient's central, peripheral, or autonomic nervous system including the brain, spinal cord, dorsal root ganglions, sympathetic chain ganglions, cranial nerves, parasympathetic nerves, and peripheral nerves, among others. The target tissue can be neurological or non-neurological tissue associated with other organs including the stomach, bladder, and intestines. The therapeutic effect comprises a plastic long-term functional change in the target tissue to lessen or eliminate a pathophysiologic disease or syndrome. The therapeutic effect can treat a plurality of neurological and non-neurological conditions including chronic and acute pain, autonomic disorder, sensory disorder, motor disorder, movement disorders, and cognitive disorder, obesity, psychiatric conditions, seizure disorders, and incontinence among others.

The neuromodulation system and method with feedback optimized electrical field generation generally includes an implantable electrode, an implantable sensor, an electrical signal generator coupled to the implantable electrode, and a controller coupled to the implantable sensor and to the electrical signal generator.

The electrical signal generator may be external or implantable in a patient. The electrical signal generator is adapted to generate an electrical noise stimulation signal for stimulating or modulating target tissue of the patient comprising neurological tissue, non-neurological tissue, or a combination of both.

The implantable electrode may comprise one or a plurality of electrodes and is implantable in or near the target tissue. The electrode receives the electrical noise stimulation signal and delivers it to the target tissue to produce an electric field in the target tissue.

The implantable sensor may comprise a single sensor or a plurality of sensors. The sensor or sensors may be incorporated with the electrode or electrodes and may be separately implantable in or near the target tissue. The sensor or sensors generate data indicative of a physical parameter associated with the target tissue. In one aspect, the sensor comprises a temperature sensor and the physical parameter of the target tissue comprises temperature. In another aspect, the sensor comprises an impedance sensor and the physical parameter of the target tissue comprises impedance.

The controller may be external or implantable in the patient. The controller is configured to receive the sensor data and in response to automatically control the electrical signal generator to generate the electrical noise stimulation signal in a way to optimize and maximize the electric field to produce an optimal therapeutic effect but with the electric field not resulting in sensor data that indicates a value of the physical parameter of the target tissue that is associated with potential damage to the target tissue.

Generally, the controller is configured to control the electrical signal generator to optimize and maximize the electric field by generating and applying an electrical noise stimulation signal that maximizes the voltage component of the electric field while maintaining a level of current density and flow to the target tissue so that the sensor data does not indicate a value of the physical parameter of the target tissue associated with potential damage to the target tissue. In one aspect, the electrical noise stimulation signal can have a peak voltage level in the range of about 5V to about 200V and current flow can be maintained in a range of about 10 mA to about 300 mA or less. The electrical noise stimulation signal can have a frequency spectrum in the range of about 50 Hz., and more preferably about 100 Hz., to about 750 KHz.

In one aspect, the electrical signal generator is adapted to generate the electrical noise stimulation signal in a frequency band having a center frequency corresponding to a peak value of impedance, and the controller is configured to control the electrical signal generator to optimize and maximize the electric field by adjusting the center frequency. In one aspect, the electrical signal generator is adapted to generate the electrical noise stimulation signal in a plurality of selectable frequency bands corresponding to a plurality of peak values of impedance, and the controller is configured to control the electrical signal generator to optimize and maximize the electric field by selecting one of the frequency bands. In one aspect, the system comprises a plurality of selectable combinations of implantable electrodes, the electrical signal generator is adapted to generate the electrical noise stimulation signal so it is received by a selected combination of the implantable electrodes, and the controller is configured to control the electrical signal generator to optimize and maximize the electric field by selecting the combination of implantable electrodes that is to receive the electrical noise stimulation signal.

The controller is configured to automatically respond to sensor data indicating a value of the physical parameter associated with potential damage to the target tissue to automatically take an action to reduce the strength of the electric field. In one aspect, the action to reduce the strength of the electric field comprises an action to reduce the current density and flow to the target tissue. In one aspect, the value of the physical parameter that is associated with potential damage to the target tissue may be a specific value of high temperature, e.g., 42° C., or a temperature range. In another aspect, the value of the physical parameter that is associated with potential damage to the target tissue may be a specific value of low impedance or an impedance range.

There has thus been outlined, rather broadly, some of the embodiments of the neuromodulation system and method with feedback optimized electrical field generation in order that the detailed description thereof may be better understood, and in order that the present contribution to the art may be better appreciated. There are additional embodiments of the neuromodulation system and method with feedback optimized electrical field generation that will be described hereinafter and that will form the subject matter of the claims appended hereto. In this respect, before explaining at least one embodiment of the neuromodulation system and method with feedback optimized electrical field generation in detail, it is to be understood that the neuromodulation system and method with feedback optimized electrical field generation is not limited in its application to the details of construction or to the arrangements of the components set forth in the following description or illustrated in the drawings. The neuromodulation system and method with feedback optimized electrical field generation is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments of the neuromodulation system and method with feedback optimized electrical field generation will become more fully understood from the detailed description given herein below and the accompanying drawings, wherein like elements are represented by like reference characters, which are given by way of illustration only and thus are not limitative of the example embodiments herein.

DETAILED DESCRIPTION

Figure 1:
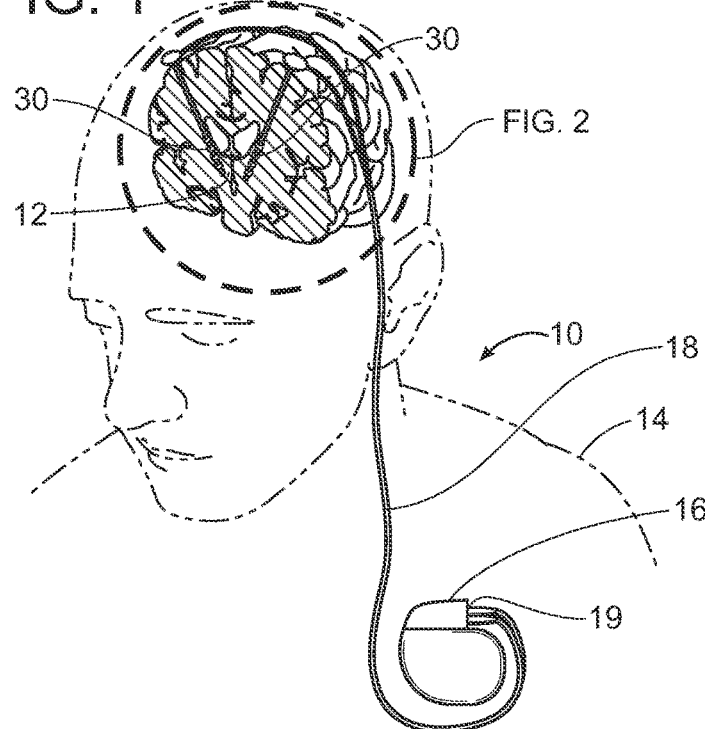
FIG. 1 is a schematic view of a neuromodulation system and method with feedback optimized electrical field generation in connection with electrical noise stimulation of target neural tissue associated with a central nervous system, more specifically target neural tissue in a brain, in accordance with an example embodiment.

A. Overview.

Example embodiments of a neuromodulation system and method with feedback optimized electrical field generation 10 (referred to herein as neuromodulation system 10) provide effective and long-lasting therapeutic results by delivering electrical noise stimulation signals to target tissue 12 of a patient 14 in such a way as to optimize and maximize the electric field in the target tissue 12 while preventing damage to the target tissue 12 and discomfort to the patient 14. By optimizing and maximizing the electric field in the target tissue 12, the system is able to produce long-term plastic functional change in the target tissue 12 with treatments that are of relatively short duration. The treatments produce effective therapeutic results that are relatively long-lasting.

The example embodiments of the neuromodulation system 10 optimize and maximize the electric field in a way that maximizes the voltage component of the electric field while maintaining a relatively low level of current density and flow in the target tissue 12, thereby helping to prevent potential damage to the target tissue 12 and patient discomfort due to heating effects. The example embodiments of the neuromodulation system 10 also rapidly and automatically respond to sensed values of physical parameters, e.g., temperature and impedance, that are associated with the target tissue 12 that indicate potential damage to the target tissue 12 by controlling the electric field to reduce its intensity, including reducing current density and flow, to prevent damage to the target tissue 12 and patient 14 discomfort.

The example neuromodulation system 10 generally includes one or more implantable electrodes 30, one or more implantable sensors S1, S2, an electrical signal generator 40 and a controller 50. The electrical signal generator 40 and the controller 50 are preferably enclosed within an implantable enclosure 16 that is adapted to be implanted in the patient 14.

The electrodes 30 and the sensors S1, S2 are implantable in, on, or around the target tissue 12 of the patient 14 to be treated. The electrical signal generator 40 is coupled to the implantable electrodes 30 and the controller 50 is coupled to the implantable sensors S1, S2 and to the electrical signal generator 40. The controller 50 is adapted and configured to control the electrical signal generator 40 to generate and deliver electrical noise stimulation signals to the target tissue 12 of the patient 14 via the electrodes 30. The electrical noise stimulation signals produce an electric field in the target tissue 12 that is optimized and maximized by maximizing the voltage component while maintaining the current density and flow at a relatively low value. Optimizing and maximizing the electric field in this way results in long-term plastic functional change in the target tissue 12 without causing damage to the target tissue 12 or discomfort to the patient 14 due to heating effects.

The sensors S1, S2 are adapted to produce sensor data comprising values of physical parameters, e.g., temperature and impedance, of the target tissue 12 as the electrical noise stimulation signals are applied to the target tissue 12. The controller 50 is adapted and configured to receive and use the sensor data to optimize and maximize the electric field for treatment. The controller 50 also is adapted and configured to rapidly and automatically respond to values of the sensor data that indicate potential damage to the target tissue 12 to control the electrical signal generator 40 to control the electric field in the target tissue 12 by reducing the intensity of the electric field, including the current density and flow.

A number of approaches for controlling the electric field to optimize and maximize its strength and to reduce its strength are disclosed. One approach includes limiting the time duration of the dose of electrical noise stimulation signals. Another approach includes generating and delivering the electrical noise stimulation signals in a relatively narrow frequency band with a center frequency corresponding to a peak value of impedance and varying or adjusting the center frequency. Another approach includes generating and delivering the electrical noise stimulation signals in a plurality of relatively narrow frequency bands with center frequencies corresponding to plurality of different peak impedance values and selecting a frequency band with a desired value of peak impedance. Another approach includes selecting from among different electrodes 30 or combinations of electrodes 30 with different spacing and orientation in relation to the target tissue 12 and thus different corresponding impedance values to deliver the electrical noise stimulation signals.

B. System in General.

FIGS. 1-10 illustrate generally an example neuromodulation system 10 that generates and delivers electrical noise stimulation signals to target tissue 12 of a patient 14 in a way that optimizes and maximizes the electric field in the target tissue 12 to provide effective long-lasting therapeutic results to the patient 14 by producing long-term plastic functional change in the target tissue 12, and that automatically responds to feedback from sensors S1, S2 to control the electric field and help prevent patient discomfort and potential tissue damage.

Figure 6:
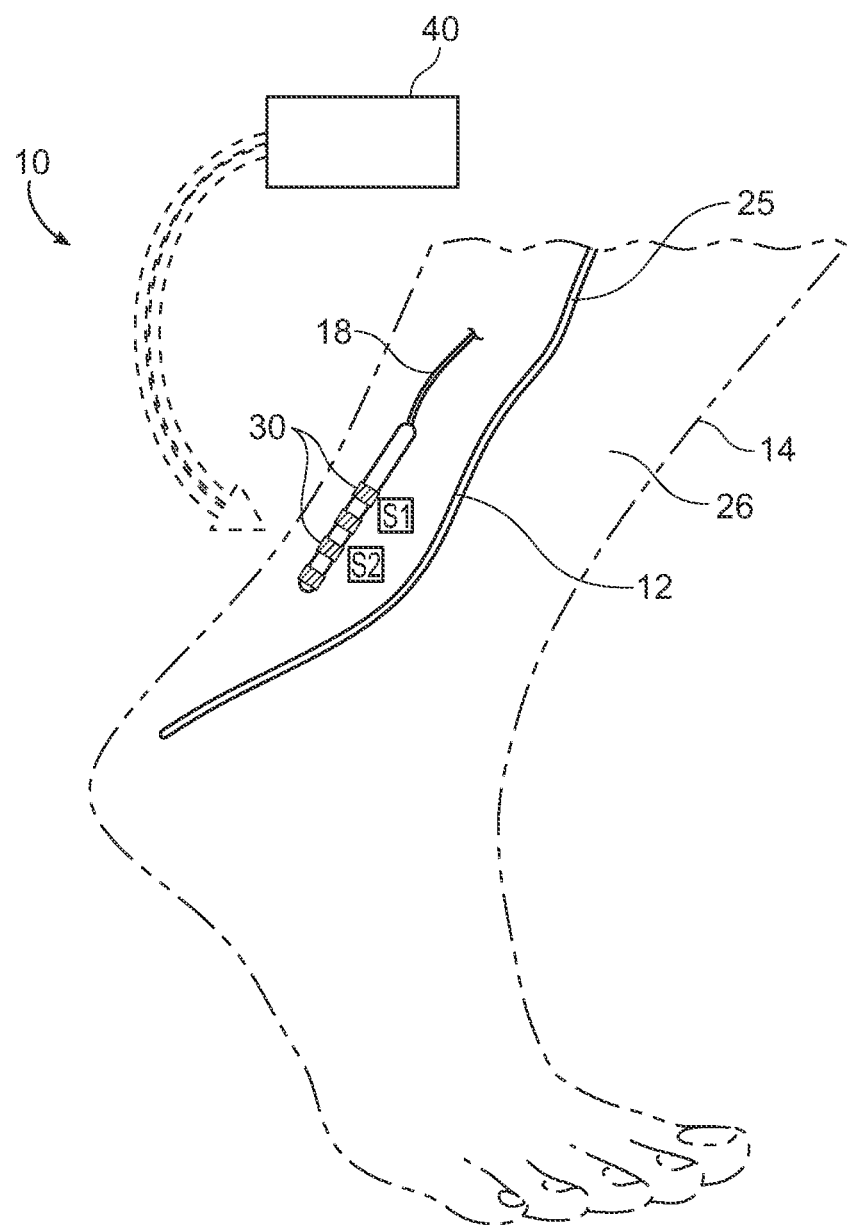
FIG. 6 is a schematic view of a neuromodulation system and method with feedback optimized electrical field generation in connection with electrical noise stimulation of target neural tissue associated with a peripheral nervous system, more specifically target neural tissue of a peripheral nerve, in accordance with an example embodiment.
Figure 7:
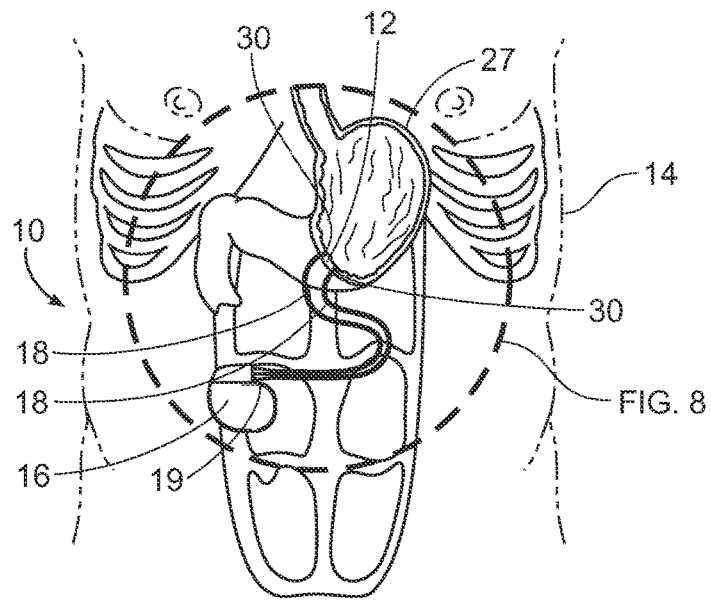
FIG. 7 is a schematic view of a neuromodulation system and method with feedback optimized electrical field generation in connection with electrical noise stimulation of target non-neural tissue associated with a gastrointestinal tract, more specifically target non-neural tissue of a stomach, in accordance with an example embodiment.
Figure 8:
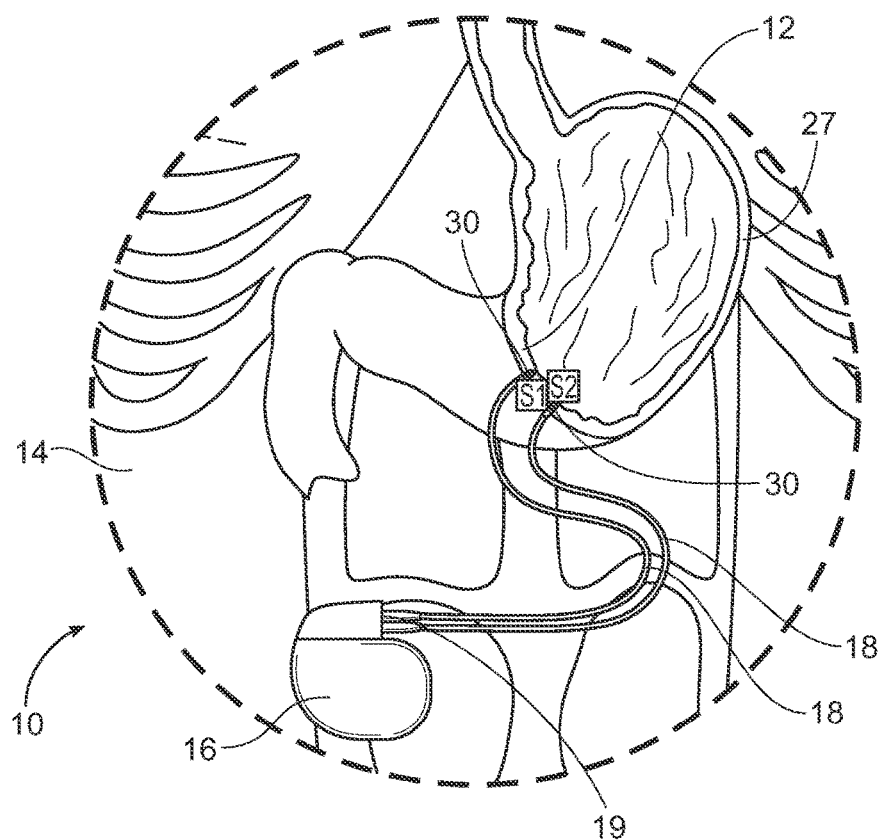
FIG. 8 is an enlargement of the portion of FIG. 7 contained within dashed lines.

In general, the example neuromodulation system 10 comprises one or more implantable electrodes 30, one or more implantable sensors S1, S2, an electrical signal generator 40 electrically coupled to the implantable electrodes 30, and a controller 50 electrically coupled to the implantable sensors S1, S2 and to the electrical signal generator 40. The electrical signal generator 40 and the controller 50 may also be implantable and may be enclosed within a suitable implantable enclosure 16 within a patient 14. Suitable electrical leads 18 may electrically couple the electrical signal generator 40 and the electrodes 30. The implantable enclosure 16 may be provided with lead connection ports 19 for that purpose. Alternatively, as illustrated in FIG. 6, the electrical signal generator 40 may be external to the patient 14 and the electrical signal generator 40 and electrodes 30 may be wirelessly coupled, for example electromagnetically via an antenna, inductively via an inductive coil, or by any other suitable wireless arrangement.

Figure 10:
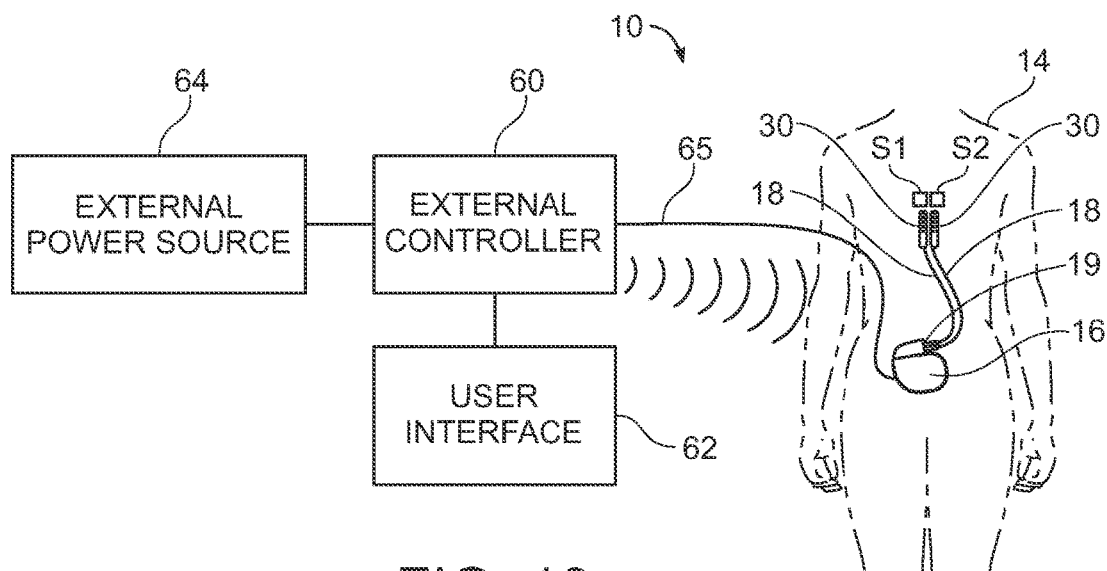
FIG. 10 is a block diagram illustrating the interconnections and communications between the major components of a neuromodulation system and method with feedback optimized electrical field generation in accordance with an example embodiment.

As illustrated in FIG. 10, the neuromodulation system 10 also can include an internal power source 52 to provide power for the controller 50 and the electrical signal generator 40, a separate external controller 60, a user interface 62, and an external power source 64. The external controller 60, if used, can be coupled to the controller 50 directly or within the implantable enclosure 16 by a percutaneous electrical lead 65 or wirelessly in any suitable manner including those identified above.

The leads 18 with electrode or electrodes 30 may be implanted in or near the target tissue 12 of the patient 14 to be treated. In some applications, the electrodes 30 also can be placed on or just under the skin of a patient at or near the target tissue 12. The sensors S1 and S2 also may be implanted in or near the target tissue 12 and may be located coincident with or near the electrodes 30.

Figure 2:
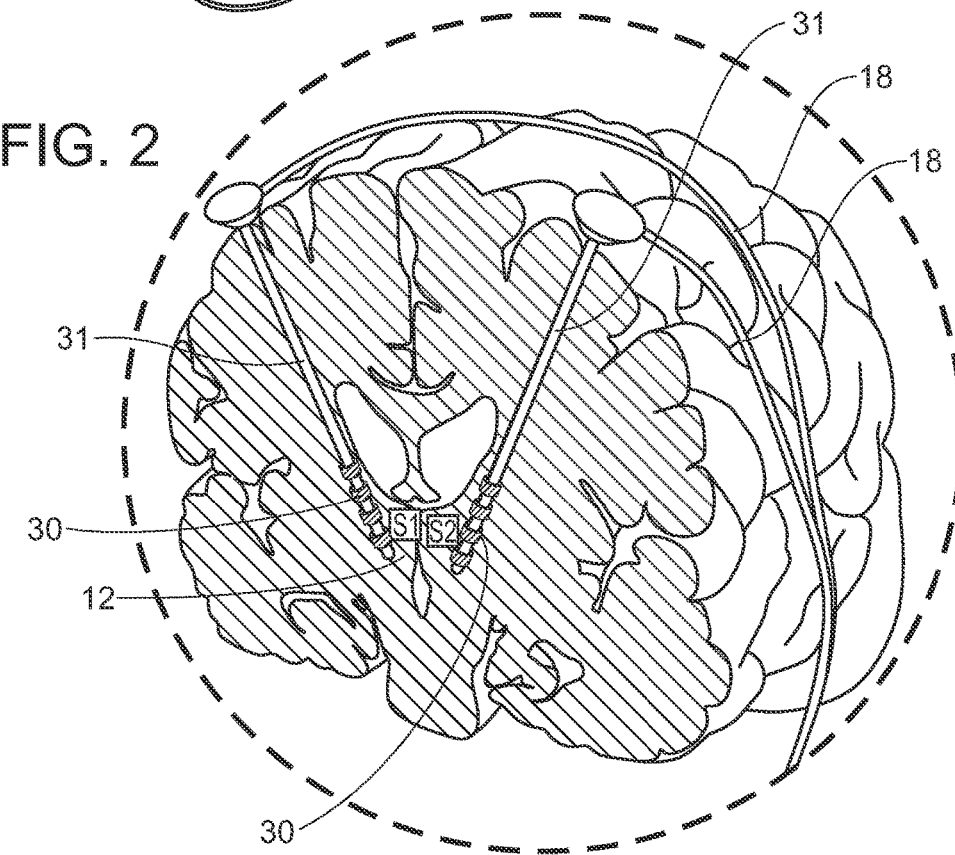
FIG. 2 is an enlargement of the portion of FIG. 1 contained within dashed lines.
Figure 3:
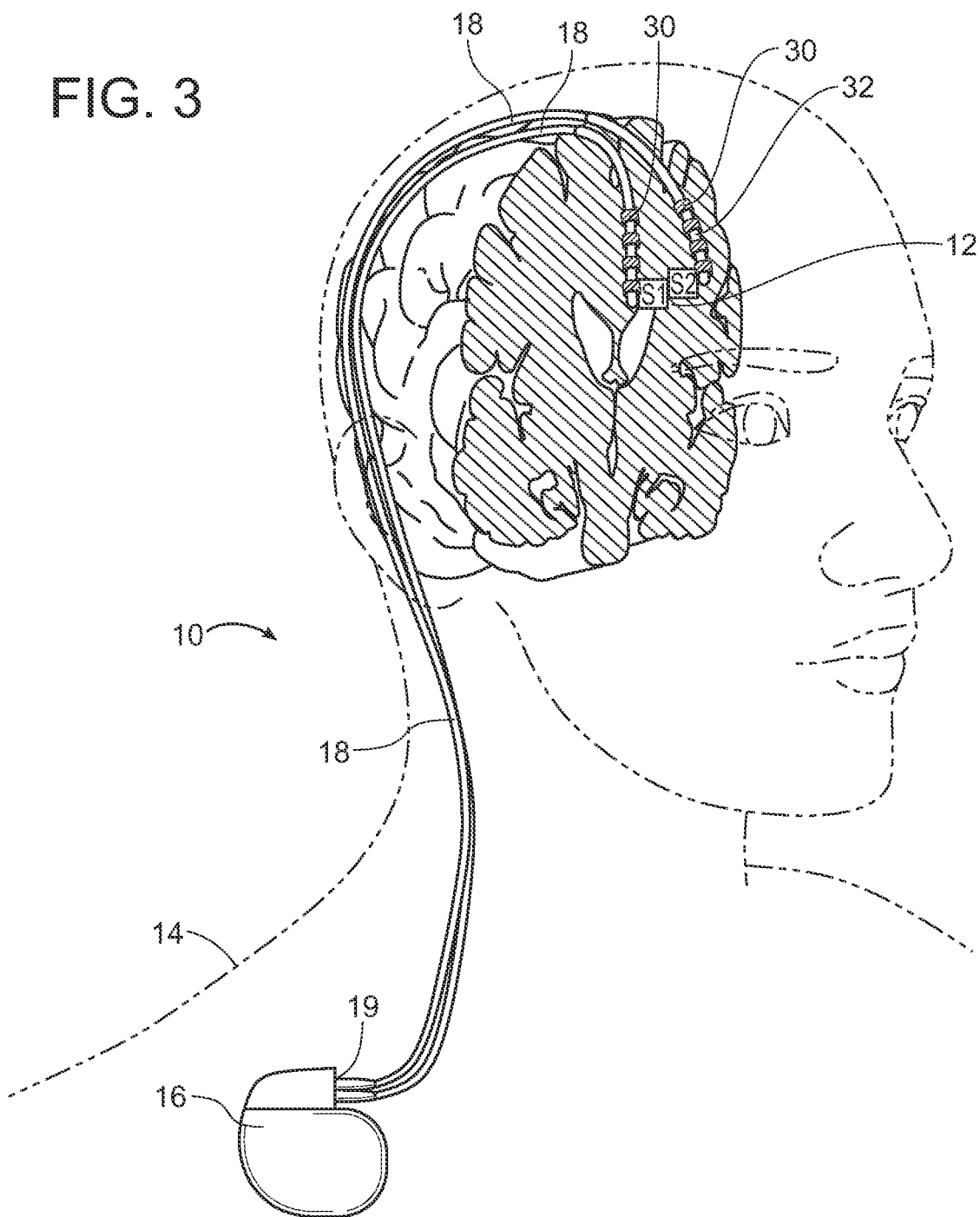
FIG. 3 is a schematic view of a neuromodulation system and method with feedback optimized electrical field generation in connection with electrical noise stimulation of target neural tissue associated with a central nervous system, more specifically target neural tissue in a brain, in accordance with another example embodiment.

As illustrated in FIGS. 1-3, in an example embodiment of the neuromodulation system 10 the target tissue 12 may comprise neural tissue of the central nervous system of the patient 14 in, on or around the patient's brain 22. For example for deep brain stimulation such as may be used to treat certain neurological conditions, the electrodes 30 are implanted relatively deep within the brain tissue. The electrodes 30 may be located near the distal ends of relatively rigid insulated wires 31 that extend from the distal ends of leads 18 such as illustrated in FIG. 2 or may be located in segmented portions 32 near the distal ends of the leads 18 as illustrated in FIG. 3, or a combination of both. The example embodiment of the neuromodulation system 10 can be used to stimulate the neural tissue in, on and around the brain 22 to treat various neurological conditions and diseases including but not limited to chronic pain, acute pain, autonomic disorders, sensory disorders, motor disorders including tremors, tics, Tourette's syndrome, and Parkinson's disease, cognitive disorders including Alzheimer's disease and dementia, depression, anxiety, psychiatric disorders including schizophrenia, seizure disorders including epilepsy, narcolepsy, incontinence, and Meniere's disease.

Figure 4:
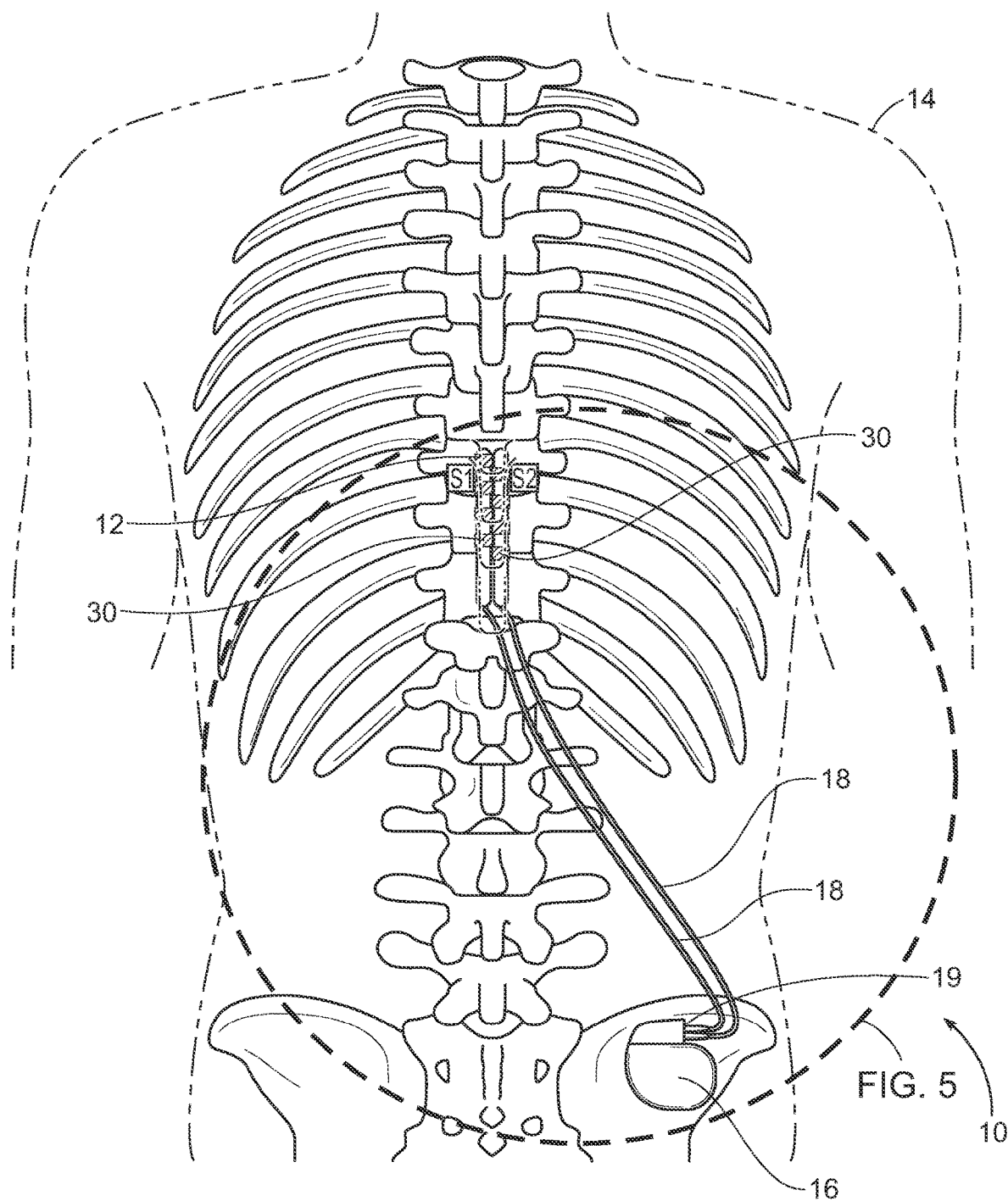
FIG. 4 is a schematic view of a neuromodulation system and method with feedback optimized electrical field generation in connection with electrical noise stimulation of target neural tissue associated with a central nervous system, more specifically target neural tissue of a spinal cord, in accordance with an example embodiment.
Figure 5:
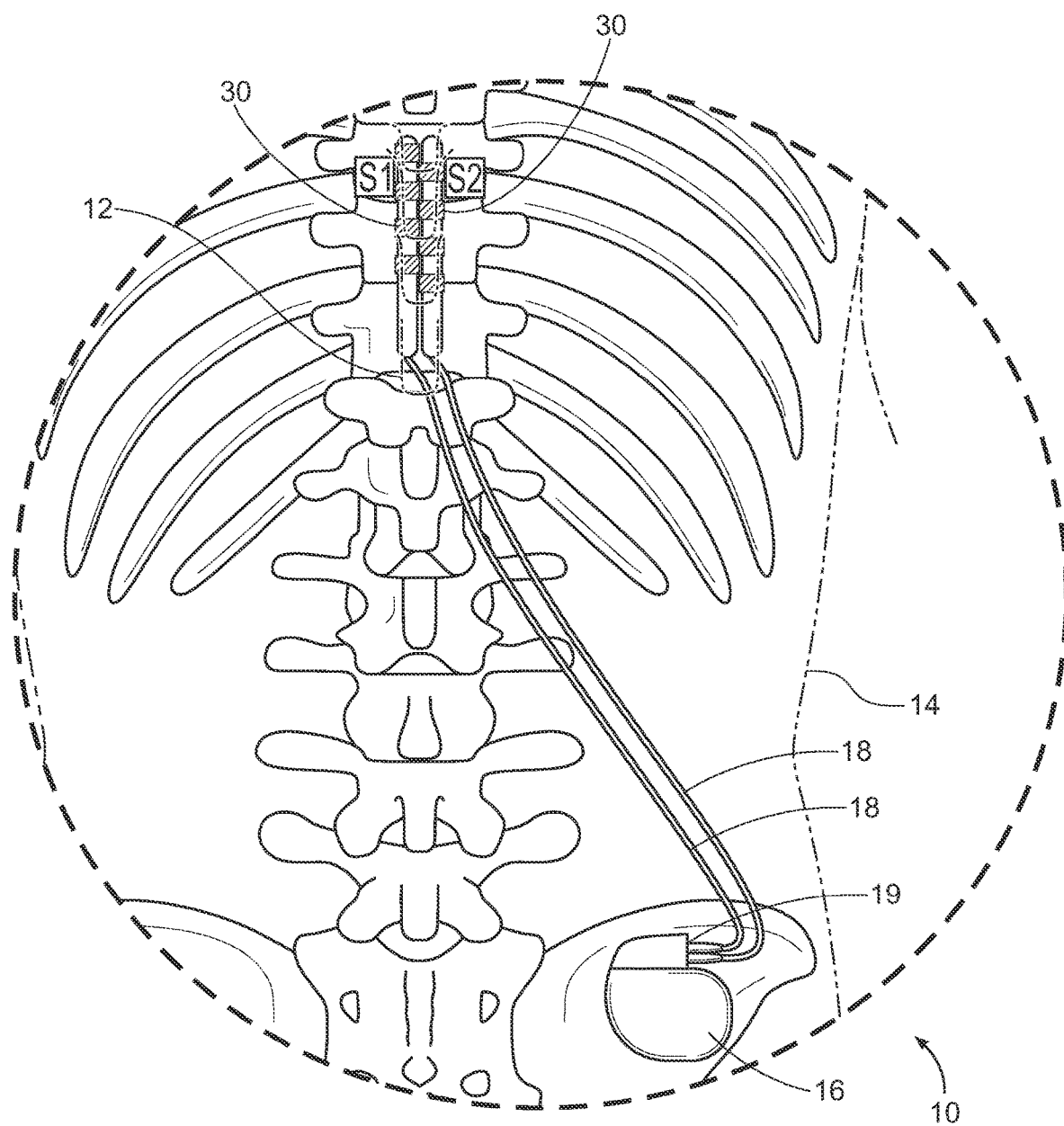
FIG. 5 is an enlargement of the portion of FIG. 4 contained within dashed lines.

In an example embodiment of the neuromodulation system 10 the target tissue 12 may comprise neural and non-neural tissue of the central nervous system of the patient 14 on and around the patient's spinal cord 24, including but not limited to neural and non-neural tissues in or around the dorsal columns, dorsal roots, dorsal roots ganglion, and ventral roots. As illustrated in FIGS. 4-5 for example, one or more leads 18 with electrodes 30 near their distal ends can be inserted into the epidural space between the bones of the spine and the spinal cord and advanced until one or more of the electrodes 30 are positioned on or adjacent to target neural and/or non-neural tissue in, on, or adjacent to the spinal cord.

The one or more electrodes 30 may be positioned at various locations laterally relative to the spinal cord including, e.g., a dorsal (posterior) region, a dorsolateral region, a lateral region, and a ventral (anterior) region, and may be positioned at various levels of the spine, e.g. S5-S1, L5-L1, T12-T1, and C8-C1, depending on the condition to be treated. The example embodiment of the neuromodulation system 10 can be used to stimulate the neural tissue in, on and around the spinal cord at various levels of the spine to treat various diseases and syndromes. For example, a lead or plurality of leads 18 with one or more electrodes 30 may be positioned within the epidural space on or adjacent to target neural tissue in, on, or around the spinal cord:

- between T7 and T12 in the thoracic spine to treat spinal lumbar pain disorders;
- between T10-T11 in the thoracic spine to provide treatment for chronic low back and leg pain;
- between C2 and T1 in the cervical spine to treat spinal cervical pain disorders;
- between C2 and T8 in the spine to treat stable or unstable angina;
- between C2 and T8 in the spine to treat abdominal pain;
- between T10-L5 in the spine to treat peripheral artery disease of the lower limbs;
- between C2 and T1 in the cervical spine to treat upper limb ischemia. A lead or plurality of leads 18 with one or more electrodes 30 may also be positioned within or near the dorsal root ganglion to treat chronic or acute pain.

Other conditions that can be treated depending on the particular target tissue stimulated and the spinal cord location and spine level of the electrodes 30 include but are not limited to acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain and fibromyalgia.

In an example embodiment of the neuromodulation system 10 the target tissue 12 may comprise neural and non-neural tissue of the peripheral nervous system of the patient 14 including tissues of the autonomic nervous system and the somatic nervous system. Target tissue 12 of the autonomic nervous system may comprise tissues of the sympathetic nervous system, e.g., the sympathetic chain ganglion and sympathetic nerves, and tissues of the parasympathetic nervous system, e.g., the parasympathetic nerves. Target tissue 12 of the somatic nervous system may comprise, e.g., the cranial nerves and the sacral nerves. The target tissue 12 also may comprise neural and non-neural tissues of the major peripheral nerves including the tibial nerves, the sacral nerves, and the sciatic nerves, as well as any other peripheral nerves.

Depending on placement of the electrodes 30 in relation to target neural and non-neural tissues of the sympathetic chain ganglion at various levels of the spine, the example embodiment of the neuromodulation system 10 can provide treatment for various conditions. For example, one or more electrodes 30 may be positioned on or adjacent to target neural tissue of the autonomic sympathetic chain anterior to the lumbar spinal column at level L1 to stimulate or modulate the nerves of the celiac plexus that connect to the pancreas, gall bladder, intestines, liver, and stomach as a treatment for pain; level L3 to stimulate or modulate the lumbar nerves that connect to the legs and feet as a treatment for pain; or level L5 to stimulate or modulate the hypogastric nerve that connects to the uterus, prostrate, bladder, rectum, and perineum as a treatment for incontinence and sexual dysfunction.

As further examples, a lead or plurality of leads 18 with one or more electrodes 30 may be positioned:

- within the sacral nerve plexus or sacral foramen to treat urinary or fecal incontinence;
- near or around the lumbar sympathetic plexus to treat chronic or acute pain of the limbs;
- near or around the celiac sympathetic plexus to treat chronic or acute pain of the abdomen;
- near or around the hypogastric sympathetic plexus to treat chronic or acute pain of the pelvic area;
- near or around the stellate ganglion to treat pain of the upper extremity;
- near or around the vagus nerve to treat seizure disorders, obesity, pain, or autonomic disorders;
- near or around a peripheral nerve to treat acute pain, chronic pain, fecal or urinary incontinence, seizure disorders, movement disorders, obesity, spasticity, and to modulate other unpleasant neurological conditions.

The electrodes 30 also may be positioned on or adjacent to other target neural and non-neural tissues of the peripheral, autonomic, and somatic nervous systems associated with the eyes, lachrymal glands, salivary glands, sweat glands, hair follicles and blood vessels of the head, neck, and arms, the heart and lungs, the stomach, duodenum, pancreas, liver, kidneys, colon, rectum, bladder, and genitalia, and the blood vessels of the lower limbs and perineum, among others. The example embodiment of the neuromodulation system 10 can thus provide treatment for various diseases and syndromes including but not limited to complex regional pain syndrome, peripheral vascular disease and chronic limb ischemia, angina pain, diabetic pain, abdominal/visceral pain syndrome, phantom limb pain, Raynaud's syndrome, hypertension, hypotension, headache and migraine, and inflammatory pain such as arthritis, irritable bowel pain, osteoarthritis pain and fibromyalgia. As further examples, a lead or plurality of leads 18 with one or more electrodes 30 may be positioned near or around somatic tissue, muscles, connective tissue, or non-neural tissue and/or near or around visceral tissue or organs, and non-neural tissue to treat acute pain, chronic pain, fecal or urinary incontinence, seizure disorders, movement disorders, obesity, spasticity, and to modulate other unpleasant neurological conditions.

In an example embodiment illustrated in FIG. 6, an electrode 30 may be implanted on or adjacent to target tissue 12 comprising a major peripheral nerve such as the tibial nerve 25 that extends down the leg 26 of a patient 16. Depending on the application and the anatomy of the patient, the electrode 30 may also be positioned on or just under the skin adjacent the target tissue 12. The electrode 30 may comprise a single electrode or may comprise multiple electrodes 30. The electrode or electrodes 30 may be positioned adjacent to the tibial nerve 25 at a desired location along its length. The electrode or electrodes 30 may be wrapped partially or completely around a section of the tibial nerve 25. The electrical signal generator 40 may be external to the patient 14 and electrically coupled to the electrode 30 wirelessly, for example electromagnetically via an antenna, inductively via an inductive coil, or via any other suitable wireless arrangement. Alternatively, the electrical signal generator 40 can be electrically coupled to the electrode 30 by a percutaneous or transcutaneous lead 18. Also alternatively, the electrical signal generator 40 can be implanted in the patient 14 along with the electrode 30. With this arrangement, the example embodiment of the neuromodulation system 10 can stimulate the target neural and non-neural tissue of the tibial nerve 25 to provide treatment for one or more diseases and syndromes including but not limited to acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, headache and migraine, cervical neuritis, post-herpetic neuralgia, vertigo, tinnitus, hearing loss and inflammatory pain such as arthritis, irritable bowel pain, osteoarthritis pain and fibromyalgia.

In an example embodiment of the neuromodulation system 10 the target tissue 12 may comprise neural and non-neural tissue of various internal organs of the patient 14. In an example embodiment illustrated in FIGS. 7-8, the target tissue 12 comprises neural and non-neural tissue of the stomach 27 of a patient 14. In this example embodiment, the electrodes 30 of the neuromodulation system 10 can be implanted in or adjacent to neural and non-neural tissue of the stomach 27, for example on or adjacent to tissues of the wall of the stomach 27. With this arrangement, the example embodiment of the neuromodulation system 10 can stimulate the neural tissue, e.g., parasympathetic nerves, and non-neural tissue, muscle tissue, of the stomach 27. The example embodiment of the neuromodulation system 10 can thus provide treatment for obesity by inhibiting or mitigating the patient's 14 sensation of hunger and/or modulating the patient's 14 gastric motor function, and/or provide treatment to help control chronic nausea and vomiting by the patient 14 associated with gastroparesis as a result of diabetes, among other conditions.

Figure 9:
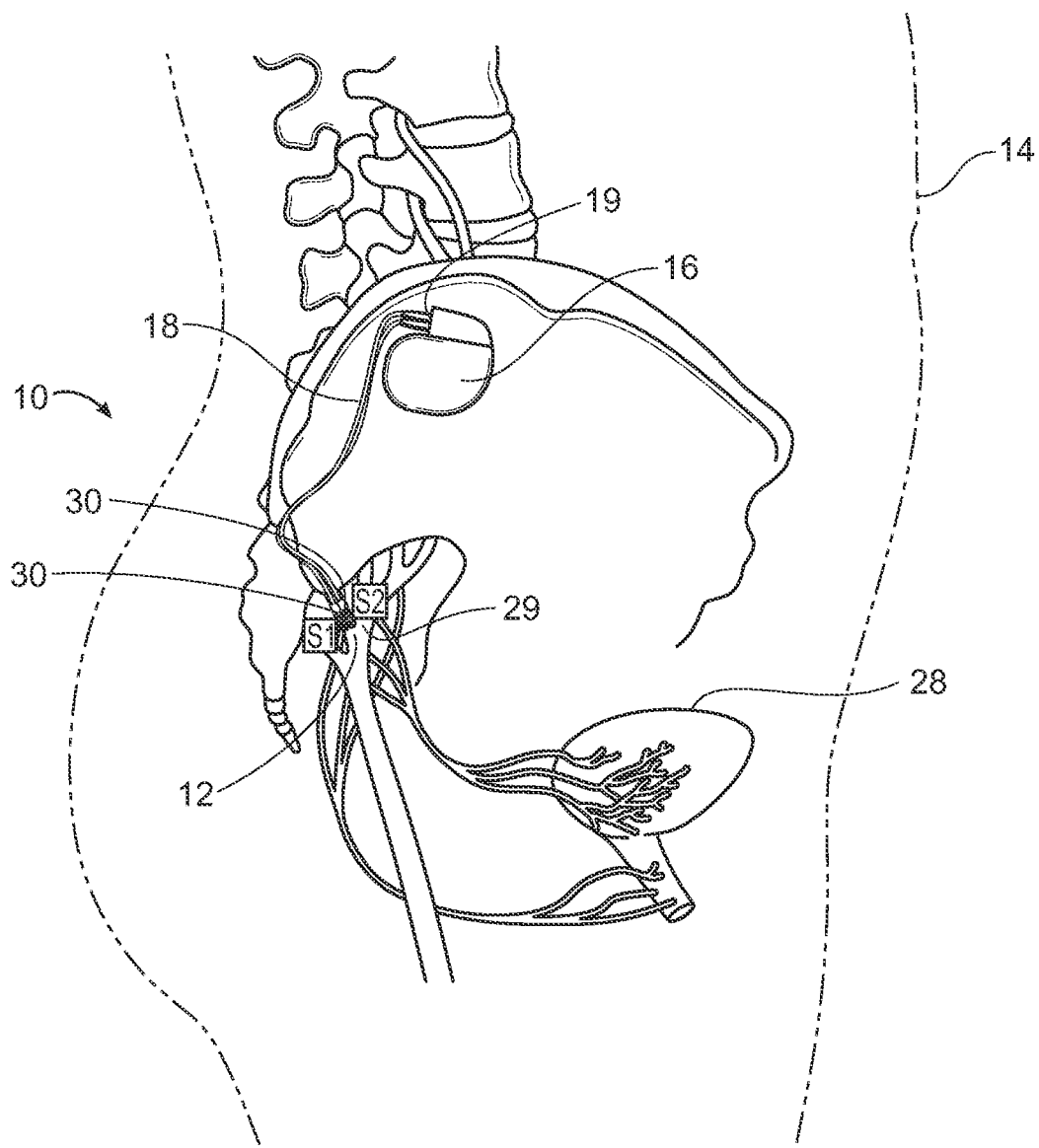
FIG. 9 is a schematic view of a neuromodulation system and method with feedback optimized electrical field generation in connection with electrical noise stimulation of target neural tissue associated with a peripheral nervous system, more specifically target neural tissue of a sacral nerve, in accordance with an example embodiment.

In an example embodiment of the neuromodulation system 10 illustrated in FIG. 9, the target tissue 12 may comprise neural and non-neural tissue associated with the bladder 28 of a patient 14, for example neural and non-neural tissue of the sacral nerves 29 associated with the bladder 28. The leads 18 and electrodes 30 of the neuromodulation system 10 may be inserted into the patient 14 percutaneously and extended through or adjacent to the sacral foramen of the patient's 14 spine until the electrodes 30 are positioned on or adjacent to the appropriate sacral nerve 29. With this arrangement, the example embodiment of the neuromodulation system 10 can stimulate the neural and non-neural tissue of the sacral nerves 29 associated with the muscles and organs, e.g., the bladder 28, sphincter, and pelvic floor muscles that relate to bladder control and thus provide treatment to the patient 14 for conditions of overactive bladder, incontinence, and others.

In each of the example embodiments of the neuromodulation system 10 described above, the electrical signal generator 40 generates electrical noise stimulation signals which are delivered to the target tissue 12 of the patient 14 by the electrodes 30 in a way that optimizes and maximizes the electric field in the target tissue 12. This is effective to provide long-lasting therapeutic results to the patient 14 by producing long-term plastic functional change in the target tissue 12. The one or more sensors S1 and S2 may be implanted in or near the target tissue 12 of the patient 14 and may be located coincident with or near the electrodes 30. As described in further detail below, the sensors S1 and S2 generate data that is indicative of a physical parameter associated with the target tissue 12. In example embodiments, the data may comprise data indicative of the temperature or impedance of the target tissue 12, or some other data indicative of the physical status of the target tissue 12. Also as described in further detail below, the sensor data is received and used by the controller 50 to optimize and maximize the electric field for treatment. The controller 50 also is configured to respond to the sensor data and to rapidly and automatically take action by controlling the electrical signal generator 40 to control and reduce the strength of the electric field as necessary to help prevent potential tissue damage and patient discomfort without the need for any direct input or feedback from the patient.

C. Implantable Electrode(s).

The electrodes 30 of the example embodiments of the neuromodulation system 10 may be implantable in the patient 14 in, on, or around the target tissue 12 to be treated. Depending on the application and the anatomy of the patient 14, the electrodes 30 may also be placed on or under the skin of the patient 14. The electrodes 30 may be electrically coupled to the electrical signal generator 40 by a suitable lead or leads 18. Alternatively, the electrodes 30 may be wirelessly electrically coupled to the electrical signal generator 40 electromagnetically via a suitable antenna, inductively via a suitable inductive coil, or by any other suitable wireless arrangement.

The electrodes 30 receive the electrical noise stimulation signals generated by the electrical signal generator 40 as described in further detail below. The electrodes 30 produce an electric field for application to the target tissue 12, which as described can include neural tissue, non-neural tissue, or a combination thereof.

The example embodiments may include a single electrode 30 or a plurality of electrodes 30. The electrodes 30 can comprise one or more electrically conductive contacts integrated in a lead 18 and electrically connected with one or more electrically conductive wires of the lead 18. The plurality of electrodes 30 can be arranged in various configurations such as illustrated in FIGS. 18A-18D and 19A-19C for example. In many cases, the electrodes 30 will be carried by and will be located near the distal ends of percutaneous leads 18, such as illustrated in FIGS. 1-2 and 19A-19C. In other cases, the electrodes 30 can be incorporated in a laminotomy or paddle lead 18, such as illustrated in FIGS. 18A-18D.

The shapes, sizes, and arrangements of the electrodes 30 and the spacing between electrodes 30 can be selected in order to generate one or more electric fields in and around the target tissue 12 having desired properties, depending at least in part on the nature and location of the target tissue, the condition being treated, and treatment being provided. The electrodes 30 can produce one or more electric fields alternately, consecutively, or simultaneously in and around the target tissue 12. In addition, and as described further below, a specific electrode 30 and/or one or more pairs or other combinations of electrodes 30 can be selected to optimize and maximize the strength or intensity of the electric field in the target tissue 12 to provide optimal therapeutic results and/or to control the strength of the electric field in the target tissue 12 to prevent discomfort to the patient 14 and damage to the target tissue 12. For example, specific electrodes 30 or pairs or other combinations of electrodes 30 having different distances from and/or different orientations, e.g., angles, with respect to the target tissue 12 can be selected, which can affect the impedance to current flow between the electrodes, the direction of current flow through the target tissue 12, the current density in the target tissue 12, and the strength and orientation of the electric field(s) in the target tissue 12. Also for example, two or more electrodes 12 on the same or separate leads can be selected and tied or used together as a single electrode with greater surface area to increase current density. See, e.g., FIG. 19A, electrodes 30c, 30g can be selected together to comprise a common cathode with electrode 30e as anode, FIG. 19B, electrodes 30a, 30c can be selected together to comprise a common cathode with electrode 30g as anode. Different electrodes 30 may also have different sizes and shapes, including surface areas, which can affect current density and flow and the strength of the electric field in the target tissue 12.

Further, the one or more electrodes 30 can be configured to function as monopolar, bipolar, or multipolar electrodes 30. For example, a pair of electrodes 30 can be configured to function in a bipolar fashion with one of the electrodes 30 acting as the anode and the other as the cathode, as illustrated in FIGS. 18A-18D and 19A-19b for example. In a particularly preferred bipolar arrangement, one of the electrodes 30 of the bipolar pair will be located in, on, or adjacent to the target tissue 12, and the other electrode 30 will be located in or on non-excitable tissue, such as fat, fascia, or myelin tissue, in order to produce an electric field in and around the target tissue 12. Alternatively, each electrode 30 of the bipolar pair can be located in tissue, including non-excitable tissue, adjacent to the target tissue 12 to produce an electric field in, through, and around the target tissue 12. Preferably, regardless of the electrode 30 locations the electric field produced will be optimized and maximized by applying to the electrodes 30 an electrical noise stimulation signal having a relatively high peak voltage, e.g., in a range of about 5V to about 200V, while maintaining an acceptable relatively low current flow, e.g., about 10 mA to about 300 mA or less, in the target tissue 12.

Figure 19A:
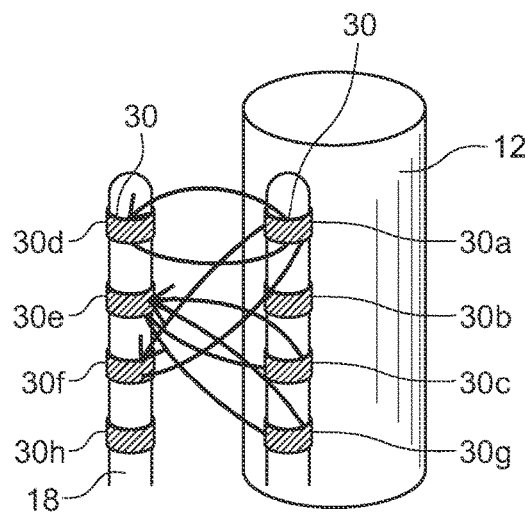
FIG. 19A is a partial perspective view graphically illustrating a selection of electrodes of a pair of percutaneous leads for application to tissue of an electrical noise stimulation signal of an implantable internal controller and noise generator of a neuromodulation system and method with feedback optimized electrical field generation in accordance with an example embodiment.
Figure 19B:
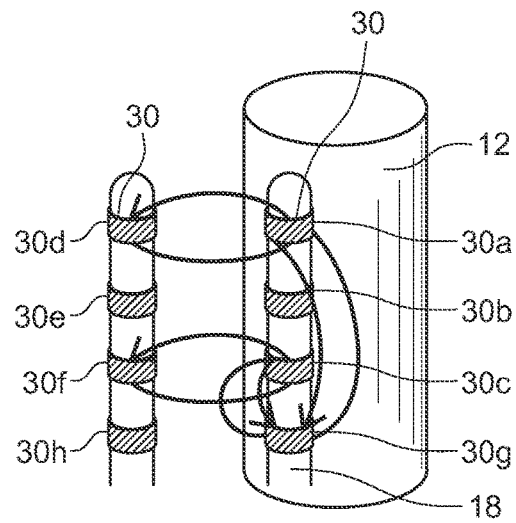
FIG. 19B is a partial perspective view graphically illustrating another selection of electrodes of a pair of percutaneous leads for application to tissue of an electrical noise stimulation signal of an implantable internal controller and noise generator of a neuromodulation system and method with feedback optimized electrical field generation in accordance with an example embodiment.

Alternatively, a plurality of electrodes 30 can function as anodes and another electrode 30 as a cathode, or vice versa, in a multipolar fashion. The various electrodes 30 functioning in a bipolar or multipolar manner can be carried on the same lead 18, as illustrated on 18A-18D and FIG. 19C, or on separate leads 18 as illustrated in FIGS. 19A and 19B, or a combination of both. Still further, one or more electrodes 30 can function as one or more monopolar cathodes located in, on, or around the target tissue 12 with another electrode 30 being positioned a substantial distance from the target tissue 12 such that most or all of the electric field is dissipated in tissues of the patient 14. Alternatively, a case of the implantable enclosure 16 can function as the anode in a monopolar configuration.

D. Implantable Sensor(s).

The one or more implantable sensors S1, S2 of the example embodiments of the neuromodulation system 10 are implantable in the patient 14 preferably in or near the target tissue 12. The sensors S1, S2 may be located coincident with or near the electrodes 30. Each of the sensors S1, S2 may comprise a separate physical unit. Alternatively, one or more of the sensors S1, S2 may be integrated together and/or with one or more of the leads 18 or electrodes 30.

Figure 11:
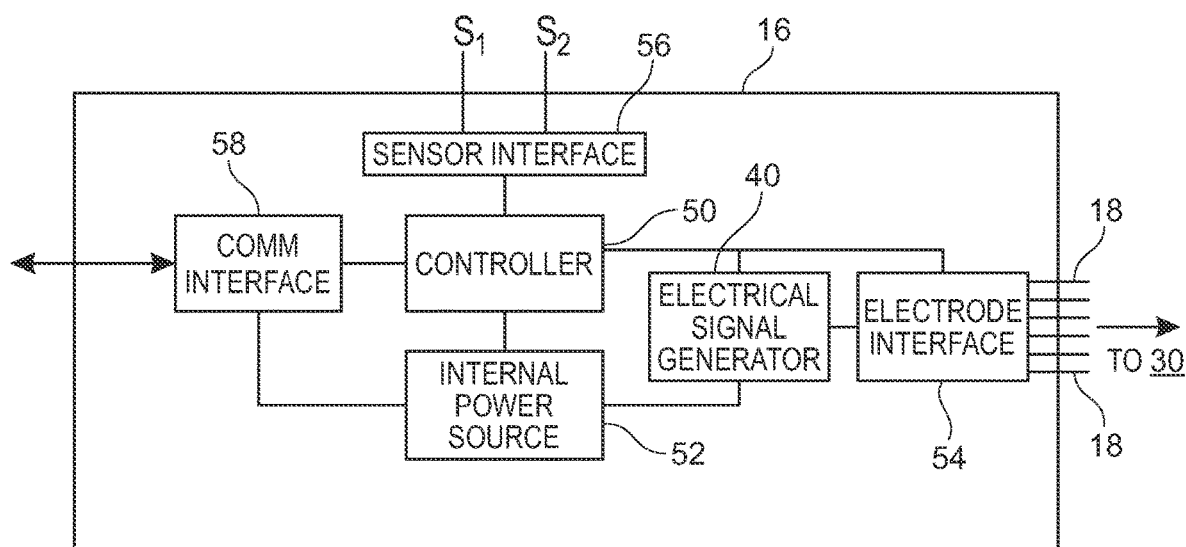
FIG. 11 is a block diagram illustrating the interconnections and communications between the major components of an implantable internal controller and noise generator of a neuromodulation system and method with feedback optimized electrical field generation in accordance with an example embodiment.

The sensors S1, S2 are preferably electrically coupled and in communication with the controller 50 via leads. The leads may comprise the leads 18 or may be separate from the leads 18. Alternatively, one or more sensors S1, S2 may be electrically coupled and in communication with the controller 50 wirelessly, for example using RF signal transmission. The sensors S1, S2 may be coupled to and communicate with the controller 50 via a sensor interface 56, which is illustrated in FIG. 11 and described in further detail below.

The sensors S1, S2 are adapted to generate sensor data that is indicative of one or more physical parameters preferably associated with the target tissue 12. The sensor data may be generated and may be communicated to the controller 50 synchronously or asynchronously, and continuously or at regular or irregular intervals of time. The sensors S1, S2 may actively communicate the sensor data to the controller 50 or the controller 50 may initiate communication with the sensors S1, S2 to retrieve the sensor data, e.g., by polling the sensors S1, S2.

In the example embodiments of the neuromodulation system 10, the sensors S1, S2 preferably comprise one or more of a temperature sensor and an impedance sensor. The temperature sensor may comprise a thermistor, a solid state temperature sensor, or any other type of temperature sensor that is suitable for use consistent with the objectives described herein. The impedance sensor may comprise a miniature impedance or conductivity sensor. The impedance sensor may comprise a solid state type sensor, such as an integrated circuit, or any other type of impedance or conductivity sensor that is suitable for use consistent with the objectives described herein.

The reason why the sensors S1, S2 preferably comprise a temperature sensor and/or an impedance sensor, and more preferably at least one of each type, is because the temperature and impedance of the target tissue 12 of a patient 14 are physical parameters of the target tissue 12 that exhibit specific values and ranges of values that provide a clear indication of the onset of potential damage and/or the occurrence of damage to the target tissue 12, and possible discomfort to the patient 14. For example, persons skilled in the art will appreciate that the types of target tissue 12 of interest in connection with the example embodiments of the neuromodulation system 10 begin to experience damage due to ablation at a temperature of about 42° C. Further, as the target tissue 12 begins to experience damage due to ablation, the impedance value of the tissue tends to rapidly decrease.

The temperature of the target tissue 12 varies in relation to the level of current density and flow in the target tissue 12 induced by application of the electric field to the target tissue 12 by the electrode 30. Thus, values and ranges of the temperature and impedance parameters provided by the sensor data that indicate potential damage to the target tissue 12 similarly indicate that the current density and flow induced by the electric field is too high. At the same time, relatively lower temperature and relatively higher impedance values and ranges indicate that the current density and flow is not at a level to potentially cause damage to the target tissue 12.

Accordingly, the example embodiments of the neuromodulation system 10 can use the temperature and impedance values of the target tissue 12 provided by the sensor data to optimize and maximize the electric field intensity to provide optimal therapeutic results while not causing damage to the target tissue 12 or discomfort to the patient 14. The example embodiments of the neuromodulation system 10 also can take action rapidly and automatically in response to temperature and impedance values indicating potential damage to the target tissue 12 or discomfort to the patient 14 to control and if necessary reduce the electric field intensity, including the current density and flow, to prevent such damage or discomfort even without any direct feedback from the patient 14. The sensors S1, S2 and the controller 50 described further below thus comprise an automatic, closed-loop feedback system.

E. Electrical Signal Generator.

The electrical signal generator 40 of the example embodiments of the neuromodulation system 10 may be implantable in the patient 14, for example within the implantable enclosure 16 as illustrated in FIGS. 1-5 and 7-11. Alternatively, the electrical signal generator 40 may be external to the patient 14 as illustrated in FIG. 6.

The electrical signal generator 40 may comprise a separate physical unit or may integrated with the controller 50 and/or with one or more other electrical or electronic components described below in connection with the electrical signal generator 40 and the controller 50. The electrical signal generator 40 also may be integrated with an external controller 60, which is described in further detail below.

The electrical signal generator 40 may be electrically coupled and in communication with the electrodes 30 via one or more electrical leads 18 as illustrated in FIGS. 1-5 and 7-10. Alternatively, the electrical signal generator 40 may be wirelessly electrically coupled to the electrodes 30 as illustrated in FIG. 6. The electrical signal generator 40 may be wirelessly coupled to the electrodes 30 electromagnetically via a suitable antenna, inductively via a suitable inductive coil, or by any other suitable wireless arrangement. The electrical signal generator 40 may be electrically coupled to the electrodes 30 via an electrode interface 54, which is illustrated in FIG. 11 and described in further detail below.

The electrical signal generator 40 may also be electrically coupled and in communication with the controller 50. The electrical signal generator 40 may be electrically coupled with the controller 50 via a wired connection or wirelessly. The electrical signal generator 40 is adapted to generate electrical noise stimulation signals for delivery to the target tissue 12 of the patient 14 through the electrodes 30 in order to produce an electric field in the target tissue 12 to stimulate or modulate the target tissue 12 and thereby produce a therapeutic result as described herein. More specifically, the electrical signal generator 40 is adapted, under control of and in response to the controller 50, to generate electrical noise stimulation signals to optimize and maximize the electric field in the target tissue 12 to produce an optimal therapeutic effect without resulting in data from the sensors S1, S2 indicating a value of the physical parameter, e.g., temperature or impedance, associated with potential damage to the target tissue 12 as described above.

The electrical signal generator 40 is preferably adapted and configurable to generate electrical noise stimulation signals having characteristics determined by parameters and commands received by the electrical signal generator 40 in real time, for example from the controller 50 or an operator, and/or determined by parameters and commands contained in an embedded or external program or storage. For example, in response to and under the control of the controller 50 the electrical signal generator 40 may be adapted and configured to start and stop the generation of the electrical noise stimulation signals so that the example embodiments of the neuromodulation system 10 can apply doses of the electrical noise stimulation signals to the target tissue 12 for selected durations of time and at selected intervals of time.

Also in response to and under the control of the controller 50, the electrical signal generator 40 is preferably adapted and configurable to selectively generate electrical noise signals that have one or more selected voltage peak values and that include all frequencies within a selected frequency spectrum or one or more selected bands of frequencies within the selected frequency spectrum with each selected band of frequencies having a selected bandwidth and center frequency. The electrical signal generator 40 also is preferably configurable to selectively generate electrical noise signals having one or more selected peak voltage levels at one or more selected frequencies within a selected frequency spectrum and/or within one or more selected frequency bands within the spectrum. The particular characteristics of the electrical noise stimulation signals the electrical signal generator 40 will be controlled to generate in practice depends on a variety of factors including the nature and location of the target tissue, the nature and severity of the condition being treated, and others. For clarity, references to "peak voltage levels" of the electrical noise stimulation signals herein are to the monopolar peak values, i.e., positive or negative peak values, of the electrical noise stimulation signals and not to their peak-to-peak values which will be about twice the peak values.

More specifically, the electrical signal generator 40 preferably is adapted to generate the electrical noise stimulation signals using one or more forms of synthesis alone or in combination comprising subtractive synthesis, additive synthesis, component modeling synthesis, wavetable synthesis, linear arithmetic synthesis, phase distortion synthesis, frequency modulation synthesis, and sample-based synthesis. Further, the electrical signal generator 40 preferably is adapted to generate the electrical noise stimulation signals to include at least one form of noise comprising Gaussian noise, white noise, pink noise, Brownian noise, red noise, and grey noise.

Also more specifically, the electrical signal generator 40 preferably is adapted and configurable to selectively generate the electrical noise stimulation signals with peak voltage values in the range of about 5V to about 200V, and over a spectrum of frequencies in the range of about 50 Hz., and more preferably about 100 Hz., to about 750 KHz. It will be appreciated that within these ranges the peak voltage values and frequencies selected for use will depend on the nature and location of the tissue being stimulated or modulated and the nature and severity of the condition being treated, among other considerations.

Alternatively, other forms of noise stimulation signals can be substituted for the electrical noise stimulation signals described above and other generators of such noise stimulation signals can be substituted for the electrical signal generator 40 to similarly stimulate the target tissue 12, provide the same or similar treatments for the same conditions, and achieve the same or comparable therapeutic effects. For example, magnetic, electromagnetic, or mechanically-induced noise, e.g., ultrasound noise, stimulation signals may be substituted for the electrical noise stimulation signals and a magnetic, electromagnetic, or ultrasound noise generator may be substituted for the electrical signal generator 40.

F. Controller.

The controller 50 of the example embodiments of the neuromodulation system 10 may be implantable in the patient 14, for example in the implantable enclosure 16 as illustrated in FIGS. 1-5 and 7-11. The controller 50 may comprise a separate physical unit or may integrated with the electrical signal generator 40 and/or with one or more other electrical or electronic components described in connection with the electrical signal generator 40 and the controller 50.

The controller 50 may comprise a general purpose microprocessor or a dedicated purpose processor such as microcontroller. The microprocessor can be a single-chip processor or implemented with multiple components. The controller 50 also may comprise computer-readable storage for storing an operating system, program code or instructions, and data and parameters for controlling the operation of the controller 50. The storage may comprise random access memory (RAM), read only memory (ROM), and/or other volatile and/or non-volatile memory types. The program code, data, etc. can also reside on a removable storage medium, for example, CD-ROM, PC-CARD, USB drives, and may be loaded or installed when needed. Using instructions retrieved from storage, the microprocessor can control the reception and manipulations of input data from components of the neuromodulaton system 10, such as the sensors S1, S2, and the output and communication of data, parameters, instructions, or commands to other components, such as the electrical signal generator 40.

The controller 50 may be coupled with and may control an electrode interface 54, which may be enclosed within the implantable enclosure 16 with the controller 50. The electrode interface 54 may comprise a separate component or may be integrated with the controller 50. The electrode interface 54 is preferably interposed between the output of the electrical signal generator 40 and the electrodes 30. The electrode interface 54 is adapted to receive the electrical noise stimulation signal from the electrical signal generator 40 as an input and to selectively connect the electrical noise stimulation signal to one or more selected electrodes 30 via one or more leads 18 as outputs. The electrode interface 54 may comprise for example a MUX or a similar controllable selector for selectively connecting an input, e.g., the electrical noise stimulation signal, to one or more selected outputs, e.g., the electrodes 30 via leads 18.

The controller 50 may be coupled with and may communicate with and receive sensor data from the sensors S1, S2 through a sensor interface 56, which may be enclosed within the implantable enclosure 16 with the controller 50. The sensor interface 56 may comprise a separate component or may be integrated with the controller 50. The sensor interface 56 is preferably adapted to receive the sensor data from the sensors S1, S2 and to pre-process it as necessary for use by the controller 50. For that purpose, the sensor interface 56 may comprise one or more data buffers, filters, and any other components necessary or desirable for receiving, cleaning, formatting, etc. the sensor data for use by the controller 50.

The controller 50 may be coupled with a communications interface 58, which may be enclosed within the implantable enclosure 16 with the controller 50. The communications interface 58 may comprise a separate component or may be integrated with the controller 50. The communications interface 58 is preferably adapted to allow the controller 50 to communicate with other components of the example embodiments of the neuromodulation system 10, such as for example the external controller 60 and user interface 62 illustrated in FIG. 10, and/or with other devices such as for example remote devices of the telecommunications network 80 illustrated in FIG. 12 and described below. The communications interface 58 preferably comprises the necessary wired and/or wireless connections, interfaces, and protocols to implement and support such communications. Suitable connections, interfaces, and protocols may include, for example, Ethernet, Wi-fi, USB, Bluetooth, as well as various other network, internet, and cellular connections, interfaces, and protocols identified below in connection with the telecommunications network 80.

The controller 50 is preferably adapted and configurable to automatically control the electrical signal generator 40 to generate and deliver the electrical noise stimulation signals to the target tissue 12 in a way that optimizes and maximizes the electric field in the target tissue 12 by maximizing the voltage component of the electric field while limiting the current density and flow in the target tissue 12 to a sufficiently low level to not generate heating effects in the target tissue 12 that may cause damage to the target tissue 12 and discomfort to the patient 14. In this way, the controller 50 is able to automatically control the electrical signal generator 40 to generate and deliver electrical noise stimulation signals that optimize and maximize the electric field in the target tissue 12 to produce an optimal therapeutic effect but without the sensor data from the sensors S1, S2 indicating a value of a physical parameter of the target tissue 12, e.g., temperature or impedance, associated with potential damage to the target tissue 12.

The present inventor has discovered that by optimizing and maximizing the electrical field produced in neural, e.g., spinal cord or nerve tissue, and non-neural, e.g., fascia or myelin, target tissue 12 in this way (high voltage-low current density and flow), larger doses of the electrical noise stimulation signals (i.e., higher voltage levels for longer periods of time) can be delivered to the target tissue 12 without causing overheating and damage to the target tissue 12. The present inventor has further discovered that this in turn produces long-term plastic functional changes in the target tissue 12 that result in a more complete neural inhibition or blockade of neural function and that last for relatively long periods of time (days-to-weeks). As a result, relatively shorter and less frequent treatments can provide essentially continuous effective therapeutic results without the need to apply electrical modulation signals very frequently or substantially continuously, and without the related need for substantially continuous device maintenance. The present inventor also has found that the target tissue 12 is less likely to develop a "tolerance" to the anatomic changes produced with repeated dosing, which is a phenomenon that plagues conventional spinal cord stimulation (SCS) systems.

In order to optimize and maximize the electric field to have the described voltage and current characteristics described, the controller 50 is preferably adapted and configurable to determine peak values of impedance to the flow of current in the target tissue 12 at one or more frequencies within a selected portion or within the entire spectrum of frequencies of electrical noise stimulation signals the electrical signal generator 40 is intended to potentially deliver to the target tissue 12 for treatment. Once the peak values of impedance and the corresponding frequencies are determined, the controller 50 can control the electrical signal generator 40 to selectively generate and deliver to the target tissue 12 electrical noise stimulation signals in one or more selected relatively narrower frequency bands having center frequencies corresponding to the peak values of impedance. The controller 50 is also configurable to control the electrical signal generator 40 to adjust the characteristics of the noise signals within a selected band, such as for example the peak voltage values of the signals, the center frequency of the band, and the width of the band. In this way, the example embodiments of the neuromodulation system 10 can optimize and maximize the electric field produced in the target tissue 12 by generating and delivering electrical noise stimulation signals with peak voltage values selected to maximize the voltage component of the electric field while maintaining the current density and flow at relatively low levels to prevent overheating and causing damage to the target tissue 12.

The controller 50 can be configured to determine the peak values of impedance and the corresponding frequencies at which they occur in any suitable manner. A number of suitable example approaches are described below. In each approach, the electrodes 30 are first inserted in the patient 14 in conventional fashion and are positioned as desired in relation to the target tissue 12 as described herein.

According to one approach, the controller 50 is preferably configurable to control the electrical signal generator 40 to generate and deliver to the target tissue 12 via the electrode 30 an electrical noise stimulation signal that has a selected peak voltage level and a selected frequency spectrum comprising the entire range of frequencies of electrical noise stimulation signals that the electrical signal generator 40 is intended to potentially deliver to the target tissue 12 for treatment.

Figure 13:
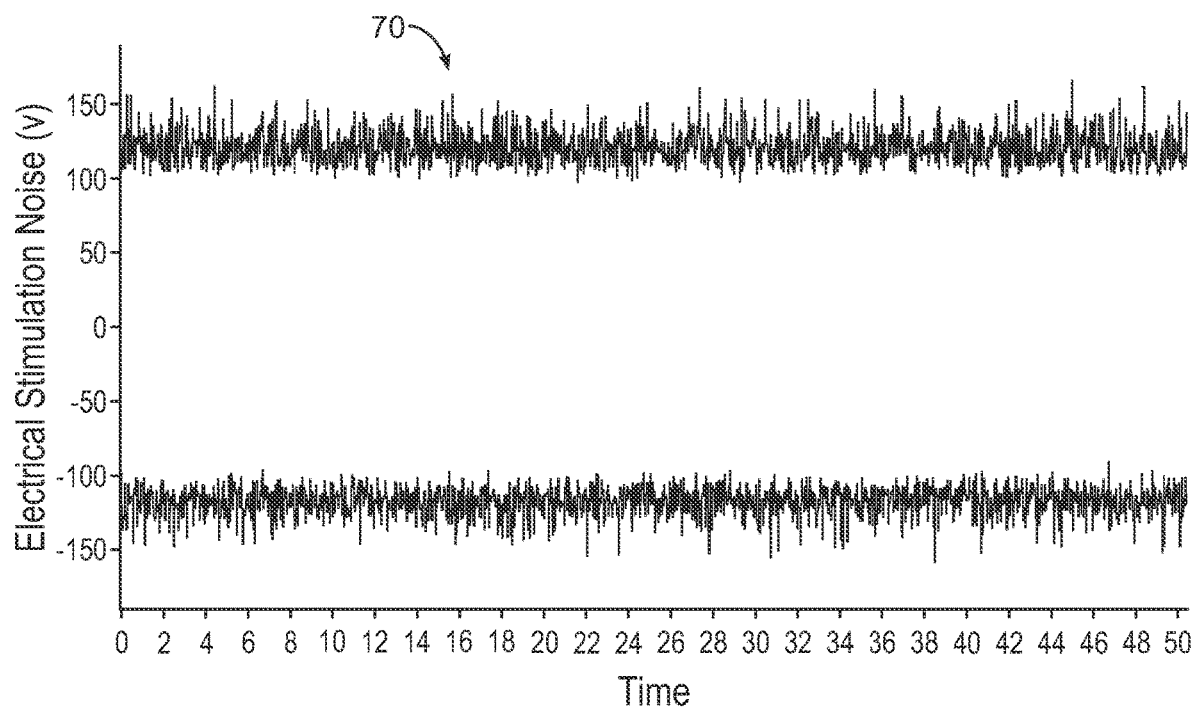
FIG. 13 is a graph illustrating the amplitude with respect to time of an electrical noise stimulation signal of an implantable internal controller and noise generator of a neuromodulation system and method with feedback optimized electrical field generation in accordance with an example embodiment.
Figure 14:
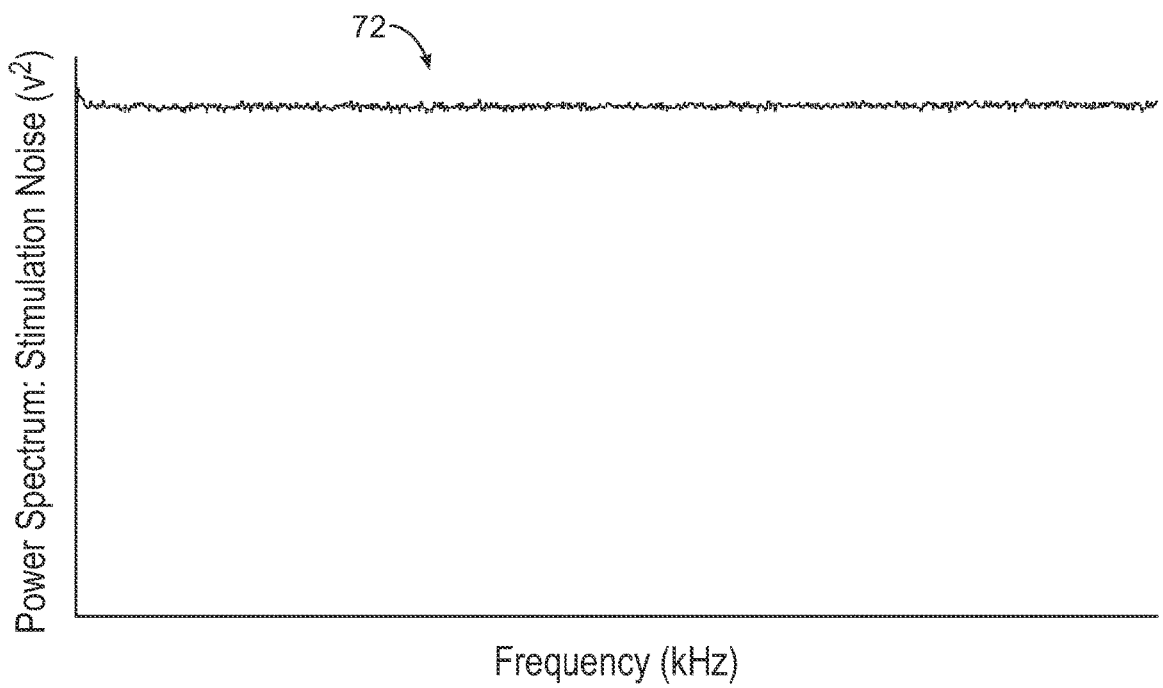
FIG. 14 is a graph illustrating the power spectrum with respect to frequency of an electrical noise stimulation signal of an implantable internal controller and noise generator of a neuromodulation system and method with feedback optimized electrical field generation in accordance with an example embodiment.

For example, as illustrated in FIG. 13, the electrical noise stimulation signal 70 can have a selected peak-peak voltage of about 300V with selected peak values of about +150V and −150V. It is noted that for clarity of illustration, FIG. 13 does not illustrate the entire electrical noise stimulation signal 70 but only illustrates the portions of the signal proximate to the peak values. As illustrated in FIG. 14, the power spectrum 72 of the electrical noise stimulation signal 70 is substantially constant over the entire frequency bandwidth.

As described herein, the frequency spectrum of the electrical noise stimulation signal 70 can be selected based on various considerations including but not limited to the nature of the tissue to be stimulated or modulated, the nature and severity of the condition or disease being treated, the locations and orientations of the electrodes 30 in relation to the target tissue, and others. As previously described, preferred bandwidths may include about 50 Hz., and more preferably about 100 Hz., to about 750 KHz.

The controller 50 is further configurable to control the electrical signal generator 40 to generate and deliver to the target tissue 12 via the electrodes 30 an electrical noise stimulation signal that comprises a band of frequencies within the selected frequency spectrum with a center frequency and a relatively narrow bandwidth. Both the center frequency and the bandwidth are selectable and can be adjusted or changed by the controller 50. The bandwidth can be selected based on the degree of resolution with which it is desired to determine the peak values of impedance and the corresponding frequencies at which they occur. For example, the bandwidth might be selected to be in the range of about 100 Hz. to about 1 KHz. Alternatively, the controller 50 can be configurable to generate and deliver a non-noise electrical stimulation signal comprising a single selectable frequency, i.e., a periodic signal.

The controller 50 is further configurable to control the electrical signal generator 40 to successively generate and deliver the electrical noise stimulation signals with the same relatively narrow bandwidth but with a plurality of different center frequencies that span a selected portion or the entire spectrum of frequencies the electrical signal generator is intended to potentially deliver to the target tissue 12 for treatment. The controller 50 can be configured to control the electrical signal generator 40 to continuously sweep or scan the center frequency across the entire frequency spectrum or a selected portion or portions of the entire spectrum, and alternatively may control the electrical signal generator 40 to adjust the center frequency in one or more fixed increments or steps. For example, the controller 50 can be configured to control the electrical signal generator 40 to continuously or discretely scan or sweep the center frequency from the lowest frequency to the highest frequency of the entire spectrum or a selected portion or portions of the entire spectrum. Alternatively, the controller 50 can be configurable to control the electrical signal generator to continuously or discretely scan a non-noise electrical stimulation signal comprising a single selectable frequency, i.e., a periodic signal, across the entire spectrum or a selected portion or portions thereof.

Figure 15A:
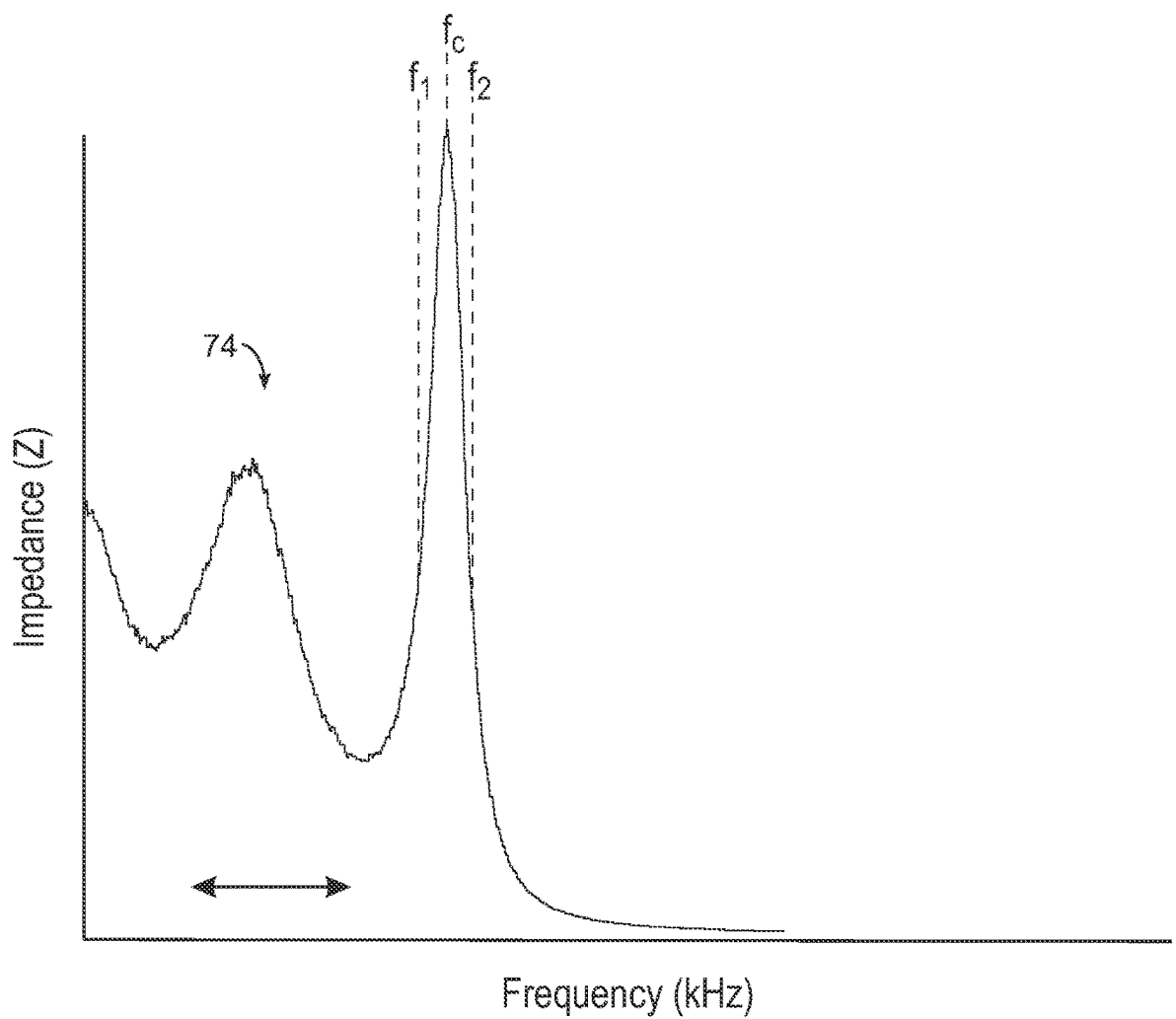
FIG. 15A is a graph illustrating an impedance amplitude spectrum with respect to frequency in response to application of an electrical noise stimulation signal of an implantable internal controller and noise generator of a neuromodulation system and method with feedback optimized electrical field generation in accordance with an example embodiment.
Figure 15B:
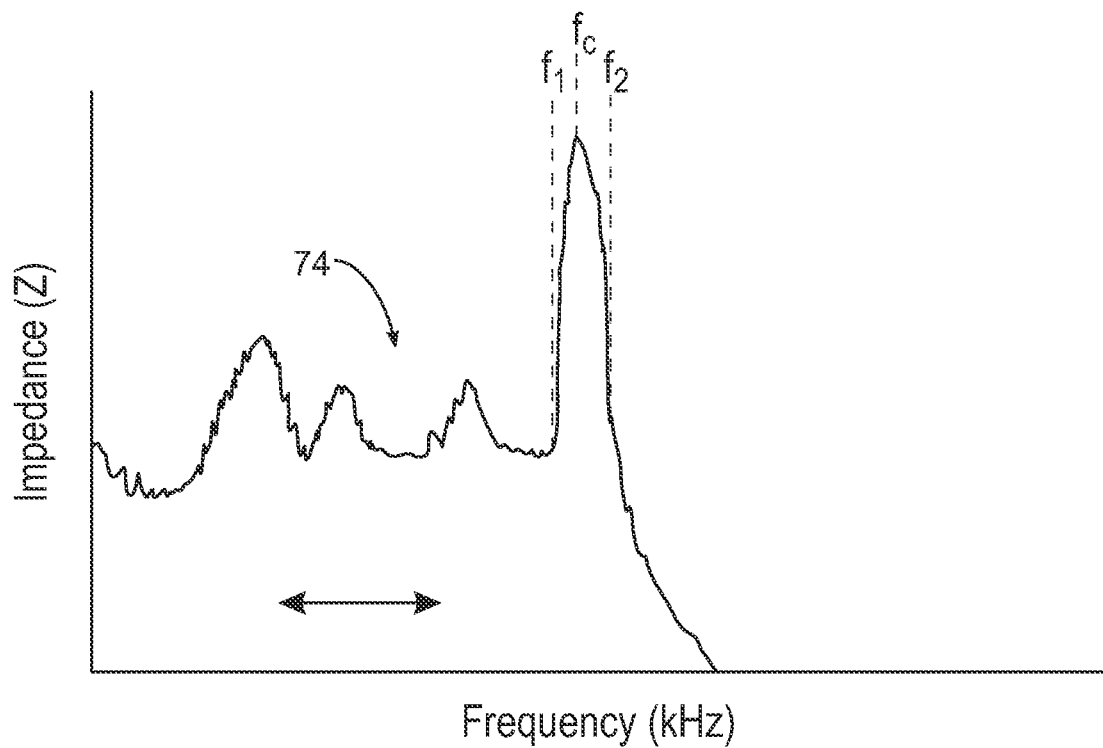
FIG. 15B is a graph illustrating another impedance amplitude spectrum with respect to frequency in response to application of an electrical noise stimulation signal of an implantable internal controller and noise generator of a neuromodulation system and method with feedback optimized electrical field generation in accordance with an example embodiment.
Figure 15C:
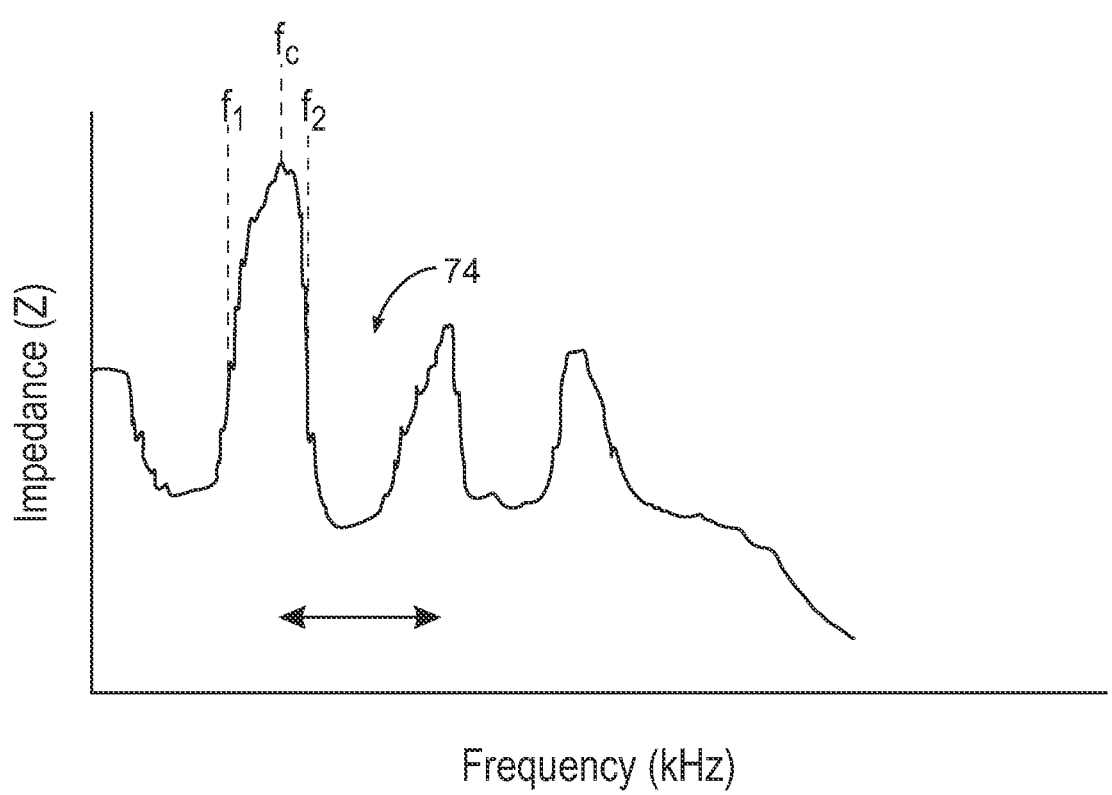
FIG. 15C is a graph illustrating yet another impedance amplitude spectrum with respect to frequency in response to application of an electrical noise stimulation signal of an implantable internal controller and noise generator of a neuromodulation system and method with feedback optimized electrical field generation in accordance with an example embodiment.

The controller 50 is configurable to receive and monitor sensor data from the sensors S1, S2 while the electrical noise stimulation signals are being delivered to the target tissue 12 via the electrodes 30. The controller 50 is configurable to determine from the sensor data the impedance to current flow in the target tissue 12 at each center frequency or at a subset of the center frequencies of the narrow band of electrical noise stimulation signals. Accordingly, the values of impedance may be substantially continuous or may be a series of discrete values. FIGS. 15A-15C illustrate several examples of the impedance (Z) 74 with respect to frequency and demonstrate how the magnitude of the impedance (Z) 74 can vary as the center frequency of the narrow band of electrical noise stimulation signals is scanned or swept substantially continuously across the selected frequency spectrum. The two-headed arrow in each figure indicates that the figure is illustrating only a portion of the values of impedance (Z) 74 for a corresponding portion of the scanned or swept frequencies in either direction.

The controller 50 is configurable to determine from the impedance (Z) sensor data a peak or peaks of greatest magnitude and the frequencies at which they occurred. The controller 50 is also preferably configurable to determine the center frequency ($f_c$) and lower and upper frequencies ($f_1$, $f_2$) for each of the peak or peaks. The center frequency ($f_c$) generally will correspond to the center frequency of the narrow frequency band of electrical noise stimulation signals that produced the peak, but may also be different for various reasons. Similarly, the lower and upper frequencies ($f_1$, $f_2$) of the peaks will generally correspond to the lower and upper frequencies of the narrow frequency bands of electrical noise stimulation signals that produce the peaks, but may also be different. The band of frequencies corresponding to a peak, like the band of frequencies of the electrical noise stimulation signals that produced the peak comprise a relatively smaller subset of the entire frequencies of the selected frequency spectrum. The upper and lower frequencies ($f_1$, $f_2$) of each peak can be determined in any number of manners, including for example treating the shape of the peak as a bandpass filtered signal and applying conventional calculations for determining filter roll-off or cut-off frequencies.

Various impedance peaks with various values of magnitude may occur at various different frequencies within the entire spectrum or range of frequencies scanned or swept. For example, FIG. 15A illustrates a first peak of impedance (Z) 74 having a first value of magnitude and a center frequency ($f_c$) at a corresponding first frequency value, FIG. 15B illustrates a second peak of impedance (Z) 74 having a second value of magnitude and a different center frequency ($f_c$) at a corresponding second frequency value, and FIG. 15C illustrates a third peak of impedance (Z) 74 having a third value of magnitude and a center frequency ($f_c$) at a corresponding third frequency value. The controller 50 preferably is configurable to discriminate between or filter the detected impedance peaks and to retain for use in providing treatment only those center frequencies and relatively narrow frequency bands corresponding to peaks with sufficient magnitudes of impedance to effectively optimize and maximize the electric field with the desired characteristics of voltage and current as described herein. For example, impedances in the range of about 200 ohms to about 10,000 ohms may be suitable for use depending on various factors including the selected value of peak voltage of the electrical noise stimulation signals to be applied, the target tissue, the nature and severity of the condition to be treated, the configuration and locations of the electrodes relative to the target tissue, and others. For clarity, it will be appreciated that the foregoing range of impedance values (Z) is contemplated to include impedance contributions of the target tissue, tissue interface, leads, and electrodes.

According to another approach to determine the peak values of impedance and the corresponding frequencies and frequency bands at which they occur, the controller 50 is preferably configurable to control the electrical signal generator 40 to generate and deliver to the target tissue 12 via the electrode 30 an electrical noise stimulation signal such as illustrated in FIGS. 13-14 that has a selected peak voltage level and a selected frequency spectrum comprising the entire range of frequencies that the electrical signal generator 40 is intended to potentially deliver to the target tissue 12 for treatment. The electrical noise stimulation signals can have the same parameters as the approach described above.

The controller 50 is configurable to receive and monitor sensor data from the sensors S1, S2 while the electrical noise stimulation signals are being applied to the target tissue 12 via the electrodes 30. The controller 50 is preferably configurable to determine from the sensor data the impedance to current flow in the target tissue 12 at one or a plurality of frequencies and frequency bands within the selected frequency spectrum. For example, the controller 50 can be configured to apply a bandpass filter to the impedance sensor data to determine the magnitude of the impedance to the electrical noise stimulation signals comprising one or a plurality of narrow frequency bands. The bandpass filter can have a selected pass band and a discretely or continuously variable center frequency. The bandpass filter may be applied to the impedance sensor data in real time or the sensor data may be stored for processing with the filter. The filter can produce a substantially continuous set of impedance values in relation to frequency similar to that shown in FIGS. 15A-15C or a set of discrete values at discrete values of frequency. The controller 50 can be configured to process the filtered impedance sensor data in a manner similar to that described above to determine the peaks in impedance, the magnitudes of the impedance at the peaks, and the corresponding frequencies and frequency bands at which they occurred for use in optimizing and maximizing the electric field to provide treatment.

It is noted that both approaches described above are examples and that the peaks and peak magnitudes of impedance and the frequencies and frequency bands at which they occur can be determined in other ways that do not depart from the broad concepts present in the example embodiments of the neuromodulation system 10 described herein. It is further noted that regardless of the approach used, it is preferred that the controller 50 monitor the sensor data from the sensors S1, S2 while the approach is being carried out. That way if the sensor data corresponding to a physical parameter, e.g., impedance or temperature, of the target tissue 12 assumes a value indicative of potential damage to the target tissue 12, for example excessive heating, the controller 50 can rapidly and automatically respond and take action by controlling the electrical signal generator 40 to control the strength of the electric field, which may include reducing current density and flow, to prevent damage to the target tissue 12 and discomfort to the patient 14. The sensors S1, S2 and the controller 50 thus comprise an automatic, closed-loop feedback control system that does not require any direct feedback from the patient 14. In addition, in order to further reduce the risk of causing damage to the target tissue 12 or patient 14 discomfort while determining the impedance peaks and peak magnitudes, the controller 50 can control the electrical signal generator 40 to generate and deliver the electrical noise stimulation signals with a peak voltage value that is less than the peak voltage value that may be used to optimize and maximize the electric field for actual treatment.

A number of example approaches to control the strength of the electric field are described in further detail below. The same approaches are equally applicable when the electrical noise stimulation signal is being applied to the target tissue 12 in advance of treatment to determine the impedance peaks and when the electrical noise stimulation signal is being applied to the target tissue 12 to provide treatment. Further, the same approaches are applicable to control the electric field to optimize and maximize its strength by maximizing the voltage component while limiting current density and flow to provide optimal treatment to the target tissue 12, and to reduce its strength, including reducing current density and flow, to prevent damage to the target tissue 12 and discomfort to the patient 14.

With reference to FIGS. 18A-18D and 19A-19C, it is also noted that in connection with determining the peaks and peak values of impedance and the frequencies at which they occur, the controller 50 is preferably configurable to control the electrode interface 54 as described above to select a plurality of different combinations of electrodes 30 to deliver the electrical noise stimulation signals or a non-noise electrical stimulation signal to the target tissue 12. As previously described, the locations, orientations, and distances of the electrodes 30 in relation to the target tissue 12 can have a substantial effect on the impedance to current flow and the strength of the electric field in the target tissue 12 in response to a particular electrical noise stimulation signal.

The controller 50 can be configured to carry out either approach described above a plurality of times using a plurality of different combinations of electrodes 30 to determine the peaks and peak values of impedance and the corresponding frequencies for each of a plurality of combinations of electrodes 30. For example, with respect to the paddle-type leads 18 and electrodes 30 illustrated in FIG. 18A-18D, the controller 50 can be configured to determine the peaks and peak values and corresponding frequencies using one, some or all of selected electrode combinations 30*a*-30*d*, 30A-30*e*, 30*a*-30*f*, 30*c*-30*d*, 30*c*-30*e*, 30*c*-30*f*, 30*b*-30*d*, 30*b*-30*e*, 30*b*-30*f*, 30*a*-30*b*, 30*a*-30*c* or other selected combinations in monopolar, bipolar, or multipolar configurations. Similarly, with respect to the percutaneous leads 18 and electrodes 30 as illustrated in FIGS. 19A-19C, the controller 50 can be configured to determine the peaks, peak values, and corresponding frequencies using one, some or all of selected electrode combinations 30*a*-30*d*, 30*a*-30*f*, 30*b*-30*e*, 30*g*-30*e*, 30*c*-30*f*, 30*a*-30*g*, 30*c*-30*g*, 30*c*/30*g*-30*e*, 30*a*-30*c*, 30*a*-30*g*, 30*a*/30*c*-30*g*, 30*b*-30*g* or other selected combinations in monopolar, bipolar, or multipolar configurations.

Figure 18A:
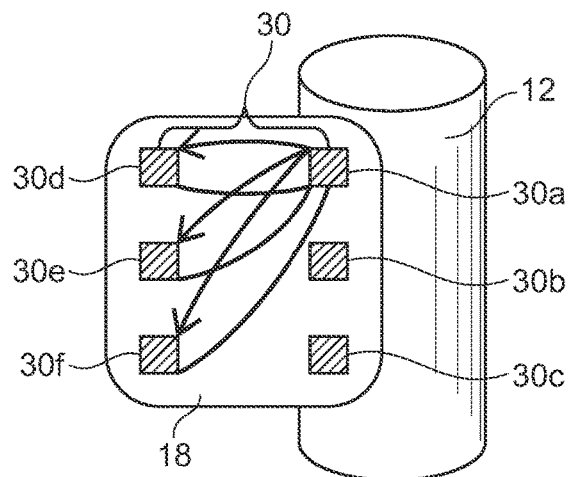
FIG. 18A is a partial perspective schematic view illustrating a selection of electrodes of a multi-electrode lead for application to tissue of an electrical noise stimulation signal of an implantable internal controller and noise generator of a neuromodulation system and method with feedback optimized electrical field generation in accordance with an example embodiment.
Figure 18B:
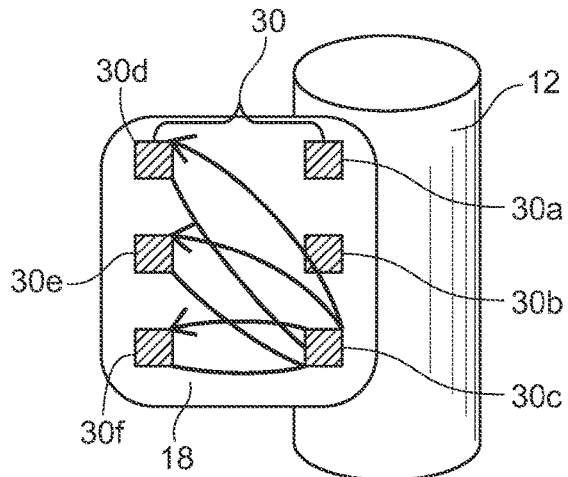
FIG. 18B is a partial perspective schematic view illustrating another selection of electrodes of a multi-electrode lead for application to tissue of an electrical noise stimulation signal of an implantable internal controller and noise generator of a neuromodulation system and method with feedback optimized electrical field generation in accordance with an example embodiment.
Figure 18C:
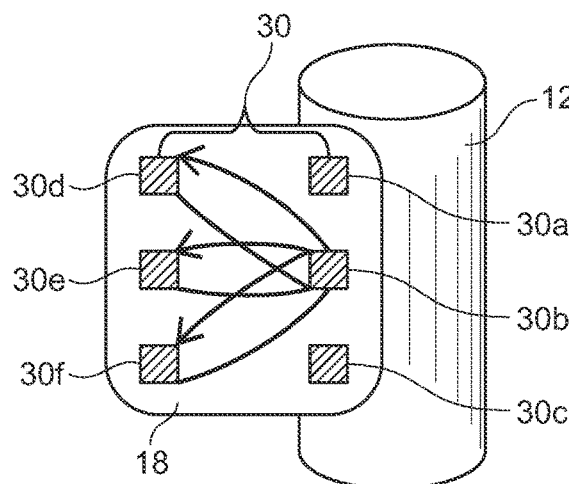
FIG. 18C is a partial perspective schematic view illustrating yet another selection of electrodes of a multi-electrode lead for application to tissue of an electrical noise stimulation signal of an implantable internal controller and noise generator of a neuromodulation system and method with feedback optimized electrical field generation in accordance with an example embodiment.
Figure 18D:
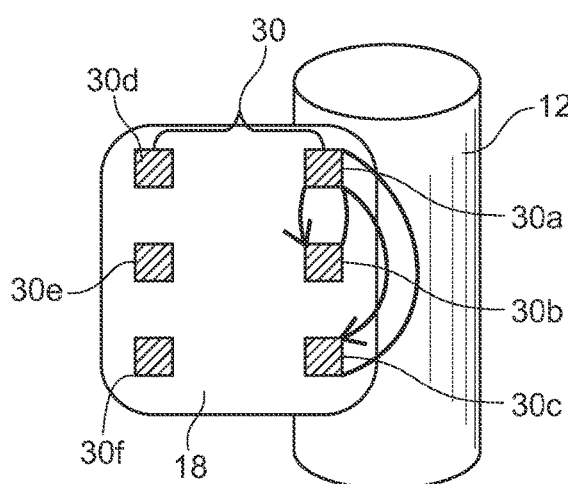
FIG. 18D is a partial perspective view graphically illustrating still another selection of electrodes of a multi-electrode lead for application to tissue of an electrical noise stimulation signal of an implantable internal controller and noise generator of a neuromodulation system and method with feedback optimized electrical field generation in accordance with an example embodiment.
Figure 19C:
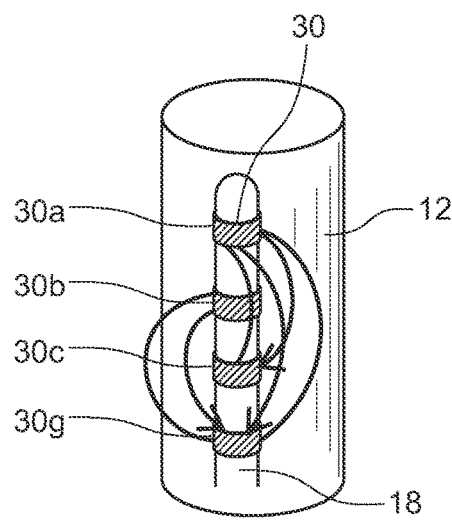
FIG. 19C is a partial perspective view graphically illustrating a selection of electrodes of a single percutaneous lead for application to tissue of an electrical noise stimulation signal of an implantable internal controller and noise generator of a neuromodulation system and method with feedback optimized electrical field generation in accordance with an example embodiment.

Further, the selected combinations of electrodes 30 may be present on different leads 18 as illustrated in FIGS. 19A-19B, and on the same leads 18 as illustrated in FIGS. 18A-18D and 19C. The selected combinations of electrodes 30 may comprise combinations with one or more electrodes 30 located in, on, or adjacent to the target tissue 12 and one or more electrodes 30 located at a distance from the target tissue 12 as illustrated in FIGS. 18A-18C and 19A-19B, e.g., in non-neural tissue such as myelin or fascia. The selected combinations of electrodes 30 may comprise combinations with all of the electrodes 30 located in, on, or adjacent to the target tissue 12 as illustrated in FIGS. 18D and 19C.

When the example embodiments of the neuromodulation system 10 are subsequently used to provide treatment, the controller 50 can be configured to use the information regarding the peaks and peak values of impedance and the corresponding frequencies at which they occurred for each of the plurality of selected combinations of electrodes 30 to select a specific combination of electrodes 30 to deliver the electrical noise stimulation signals to the target tissue 12 that will optimize and maximize the electric field in the target tissue 12 with the desired voltage and current characteristics described herein to produce optimal therapeutic results. This can be done either under operator control or automatically by the controller 50.

To provide treatment to a patient 14, the controller 50 can be configured to control the electrical signal generator 40 to optimize and maximize the electric field in the target tissue 12 with the desired voltage and current characteristics to provide optimal therapeutic results without the sensor data indicating potential damage to the target tissue 12 in a number of ways. In one example approach, the controller 50 can be configured to control the electrical signal generator 40 to limit the dose of the electrical noise stimulation signals and thus the electric field to the target tissue 12 by limiting the duration of time the electrical signal generator 40 delivers the electrical noise stimulation signals with peak voltage values in the preferred range described herein to the target tissue 12. This in turn limits the current density and flow over time and limits heating of the target tissue 12, thus producing optimal therapeutic effects without the sensor data indicating a value of the physical parameter, e.g., temperature or impedance, associated with potential damage to the target tissue 12 or discomfort to the patient 14. For example, the present inventor has found that in some instances electrical stimulation signals with peak voltage values in the preferred range can be delivered to the target tissue 12 to produce an optimized and maximized electric field in doses as short as four (4) minutes and provide effective relief from pain for up to a week or more without causing any damage to the target tissue 12 or discomfort to the patient 14.

In another example approach, the controller 50 can be configured to optimize and maximize the electric field in the target tissue 12 by controlling the electrical signal generator 40 to generate and deliver the electrical noise stimulation signals to the target tissue 12 in one of the narrow frequency bands of the plurality of narrow frequency bands previously determined to correspond to peak values of impedance of the target tissue 12. Further, the controller 50 can be configured to control the electrical signal generator 40 to adjust the center frequency of the frequency band upwardly or downwardly to further control and adjust the electric field and to monitor the sensor data to determine the effects of the adjustments on the impedance, voltage, current density and flow, and temperature of the target tissue 12 to optimize and maximize the electric field in the target tissue 12.

In another example approach, the controller 50 can be configured to optimize and maximize the electric field in the target tissue 12 by selecting a first frequency band corresponding to a first peak value of impedance of the target tissue 12 from the plurality of frequency bands previously determined to correspond to peak values of impedance of the target tissue 12. The controller 50 can be further configured to control the electrical signal generator 40 to generate and deliver the electrical noise stimulation signals to the target tissue 12 in the selected first frequency band. The controller 50 can further be configured to monitor the sensor data, make a determination regarding the characteristics of the electric field produced in the target tissue 12 by the electrical noise stimulation signals in the first frequency band, select a second frequency band corresponding to a second peak value of impedance of the target tissue 12, and control the electrical signal generator 40 to generate and deliver the electrical noise stimulation signals to the target tissue 12 in the selected second frequency band. The controller 50 can be configured to continue to select additional frequency bands corresponding to previously determined peak values of impedance and control the electrical signal generator 40 to generate and deliver electrical noise stimulation signals in each of the selected bands until the most optimized electric field, e.g. highest voltage component with acceptably low current density and flow, is produced in the target tissue 12.

In another example approach, the controller 50 can be configured to control the electrode interface 54 to select a first electrode 30 or combination of electrodes 30 from the plurality of electrodes 30 and plurality of possible combinations of electrodes 30 as described above. The controller 50 can be further configured to control the electrical signal generator 40 to generate the electrical noise stimulation signal and deliver it to the target tissue 12 via the first selected electrode 30 or combination of electrodes 30 to produce the electric field in the target tissue 12. The controller 50 can further be configured to monitor the sensor data, make a determination regarding the characteristics of the electric field produced in the target tissue 12 using the first selected electrode 30 or combination of electrodes 30, select a second electrode 30 or combination of electrodes 30, and control the electrical signal generator 40 to generate and deliver the electrical noise stimulation signals to the target tissue 12 using the second electrode 30 or combination of electrodes 30. The controller 50 can be configured to continue to select additional electrodes 30 or combinations of electrodes 30 to deliver the electrical noise stimulation signals to the target tissue 12 until the most optimized electric field, e.g. highest voltage component with acceptably low current density and flow, is produced in the target tissue 12.

It will be appreciated that any one or more of the above-described approaches, as well as others, can be employed alone or in combination. It will also be appreciated that the controller 50 can also be configured to control the electrical signal generator 40 to change or adjust the peak voltage values of the electrical noise stimulation signals in combination with any one or more of the above-described or other approaches.

It also will be appreciated from the foregoing descriptions of example approaches to optimize and maximize the electric field that the controller 50 is adapted and configured to optimize and maximize the electric field automatically in response to the sensor data even without any direct feedback from the patient 14. In addition and if desired, an operator or user of the example embodiments of the neuromodulation system 10 can further adjust the optimized electric field based on subjective input regarding patient 14 sensations in response to application of the automatically optimized electric field to the target tissue 12 in order to optimize the sensations as subjectively felt by the patient 14 and the patient's subjective treatment experience. For example, an operator or user can have a patient 14 being treated compare and describe the sensations the patient 14 is subjectively feeling as the center frequency of a selected frequency band is adjusted, as different frequency bands are selected, and/or as different combinations of electrodes 30 are selected. The operator or user can then provide corresponding inputs to the controller 50 to control the electrical signal generator 40 to adjust the parameters of the electrical noise stimulation signals and/or to adjust the selection of electrodes 30 in order to adjust the electric field produced in the target tissue 12 and optimize the patient's subjectively felt sensations and treatment experience.

Further with regard to optimizing and maximizing the electric field, the controller 50 is preferably configured to control the electrical signal generator 40 to generate the electrical noise stimulation signals with peak voltage values in the range of about 5V to about 200V over a frequency spectrum of about 50 Hz., and more preferably about 100 Hz., to about 750 KHz. Within each range, the values of peak voltage and the frequencies selected for treatment will depend on the nature and location of the tissue being stimulated or modulated and the nature and severity of the condition being treated, among other considerations.

Still further, within the foregoing voltage and frequency ranges, the controller 50 also is preferably configured to control the electrical signal generator 40 to generate and deliver the electrical noise stimulation signals to produce optimized and maximized electric fields in the target tissue 12 having intensity values in the range of about 1,000V/m to about 500,000V/m with current flow in the range of about 10 mA to about 300 mA or less.

As described above, the controller 50 is preferably configured to monitor the sensor data produced by the sensors S1, S2 both while the electrical noise stimulation signals are being provided to the target tissue 12 to determine the peaks and peak values of impedance and to stimulate or modulate the target tissue 12 to provide treatment. The controller 50 is preferably configured to rapidly and automatically respond to the sensor data indicating a value of the physical parameter, e.g., impedance and/or temperature, associated with potential damage to the target tissue 12 and to rapidly and automatically take an action to control and reduce the strength of the electric field, and/or reduce the current density and flow, to prevent damage to the target tissue 12 and discomfort to the patient 14. Thus, as noted previously, the sensors S1, S2 and the controller 50 comprise an automatic, closed-loop feedback system that does not require direct feedback from the patient 14.

Figure 16:
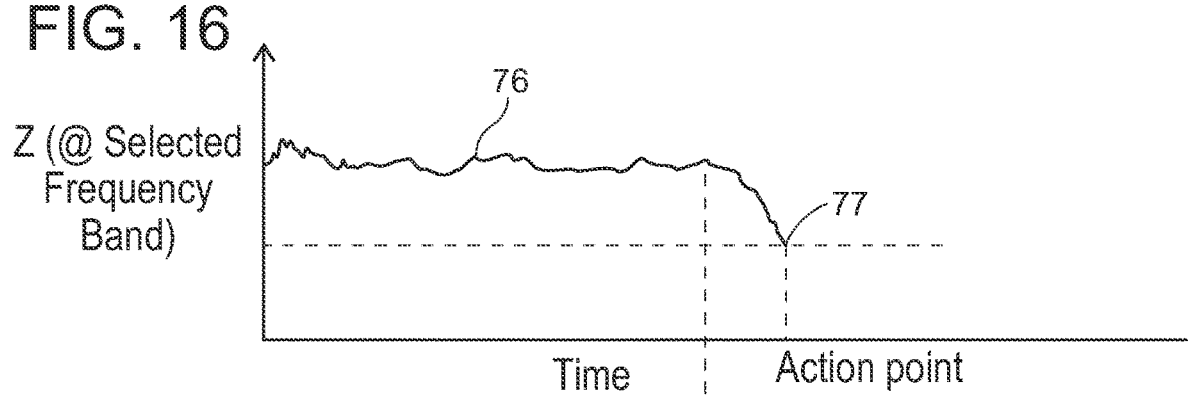
FIG. 16 is a graph illustrating impedance amplitude with respect to time in response to application of an electrical noise stimulation signal of an implantable internal controller and noise generator of a neuromodulation system and method with feedback optimized electrical field generation in accordance with an example embodiment.
Figure 17:
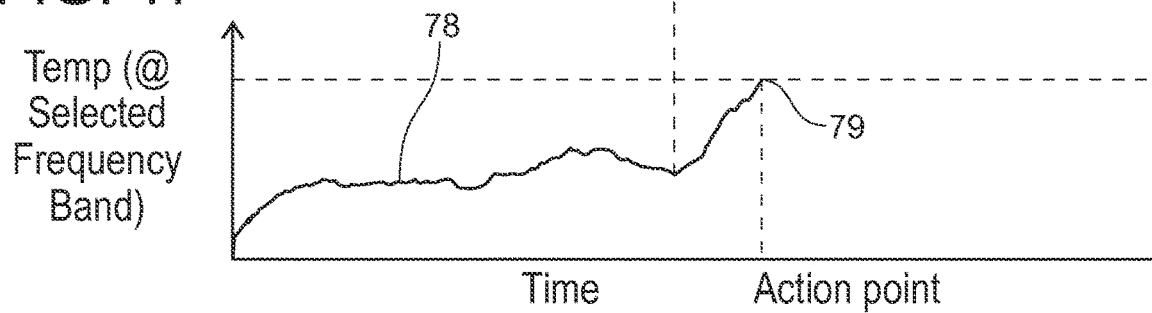
FIG. 17 is a graph illustrating temperature with respect to time in response to application of an electrical noise stimulation signal of an implantable internal controller and noise generator of a neuromodulation system and method with feedback optimized electrical field generation in accordance with an example embodiment.

For example, as illustrated in FIG. 16-17 while the electrical noise stimulation signals are being applied to the target tissue 12 in a selected frequency band, the value of the monitored impedance (Z) 76 derived from the sensor data produced by one or more of the sensors S1, S2 may be expected to remain relatively stable. Similarly, the value of the monitored temperature 78 of the target tissue 12 derived from the sensor data produced by one or more of the sensors S1, S2 may be expected to remain relatively stable and perhaps to rise somewhat with larger doses, e.g., longer durations or higher peak voltage values, of the electrical noise stimulation signals. However, if or when the value of the monitored temperature 78 rises to a predetermined level or value indicative of potential damage to the target tissue 12 as illustrated by the horizontal dashed line in FIG. 17, a temperature action point 79 is reached. Similarly, if or when the value of the monitored impedance 76 decreases to a predetermined level or value indicative of potential damage to the target tissue 12 as illustrated by the horizontal dashed line in FIG. 16, an impedance action point 77 is reached. The controller 50 is configurable to determine when an action point has been reached and to rapidly and automatically take action as described herein.

The predetermined level or value of temperature that corresponds to a temperature action point 79 can be a predetermined relative or absolute value, such as 42° C., or a range of temperatures, or another derived parameter of temperature such as an average, mean, or slope. Similarly, the predetermined level or value of impedance that corresponds to an impedance action point 77 can be a predetermined absolute or relative value, such as a 50% decrease, or a range of absolute or relative impedance values, or another derived parameter of impedance such as an average, mean, or slope.

Typically, it can be expected that a relatively rapid rise in the value of temperature and a relatively rapid decrease in the value of impedance will correspond in time and together indicate potential damage to the target tissue 12, but not always. Accordingly, the controller 50 may be configured to monitor and use the sensor data values for either physical parameter, but preferably both, in determining whether and when to take action.

Regarding the actions the controller 50 may take to control the strength of the electric field or the current density and flow to prevent damage to the target tissue 12 and discomfort to the patient 14, it will be appreciated that any one or more or a combination of the above-described actions for controlling the electric field to optimize and maximize it can also be used to control the electric field to reduce its strength, including reducing the current density and current flow in the target tissue 12. Thus, any one or more or a combination of such approaches, e.g., adjusting center frequency, selecting different frequency bands, and selecting different electrodes, can comprise the action or actions taken by the controller 50 in response to the sensor data indicating a value of the physical parameter, e.g., temperature and impedance, associated with potential damage to the target tissue 12.

G. User Interface.

Figure 12:
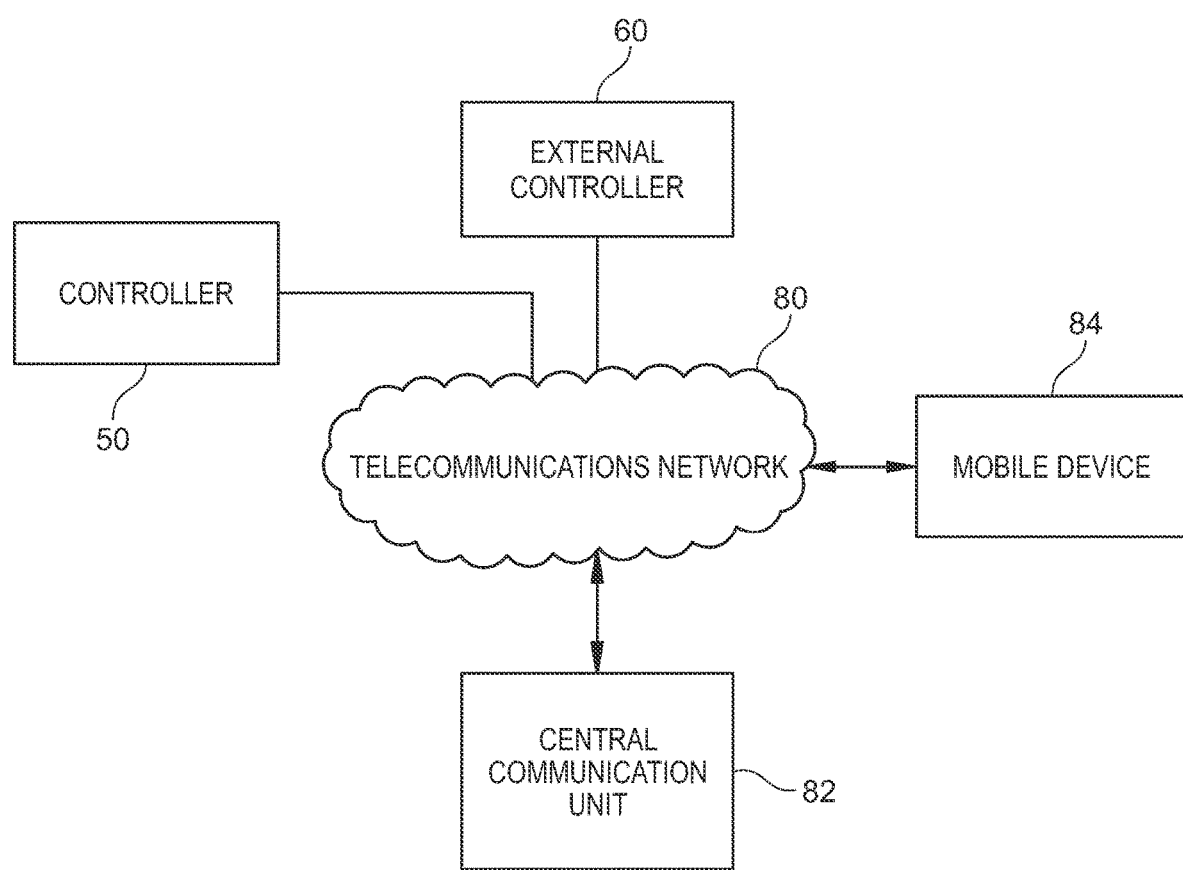
FIG. 12 is a block diagram illustrating the interconnections and communications between an implantable internal controller and an external controller of a neuromodulation system and method with feedback optimized electrical field generation in accordance with an example embodiment in connection with an external telecommunications network.

As illustrated in FIG. 10, the example embodiments of the neuromodulation system 10 may but need not necessarily include a user interface 62 external to the patient 14. If included, the user interface 62 may comprise a conventional computer or computer system, and/or one or more peripherals, such as a conventional display, keyboard, keypad, and pointing device, such as a mouse. The user interface 62 also may comprise a mobile device 84, such as a tablet computer, as illustrated in FIG. 12. The user interface may be adapted and configured to enable a user or operator to interact with the controller 50 either directly or indirectly via an external controller 60, which is described further below. The user interface 62 may comprise a separate unit or component and may be integrated in whole or in part with the external controller 60.

The user interface 62 can be used to communicate with the controller 50 and with the external controller 60 to enable powering the example embodiments of the neuromodulation system 10 up and down, to perform system setup, to enter start/stop commands for generation of the electrical noise stimulation signals, to make adjustments to the parameters and characteristics of the electrical noise stimulation signals either for future use or in real time, and to otherwise enable user or operator control of the example embodiments of the neuromodulation system 10. The user interface 62 also can be adapted and configured to receive and display various items of information to enable a user or operator to monitor the status, operation and functionality of the example embodiments of the neuromodulation system 10 and if necessary intervene. Such information can include, for example, sensor data, such as temperature and impedance values, identification of the selected electrodes, and various characteristics of the electrical noise stimulation signal, such as voltage level, current intensity level, field intensity, center frequency, and frequency bandwidth. Such information also can include treatment information including the dose time selected and the time remaining. The information also can include information concerning system status such as the remaining charge level of batteries comprising an internal power source 52, which is described further below, internal temperature of the implantable enclosure 16, etc.

H. External Controller.

As illustrated in FIG. 10, the example embodiments of the neuromodulator system 10 may but need not necessarily include an external controller 60 that is external to the patient 14. If included, the external controller 60 may comprise a conventional computer or computer system, and may also comprise a mobile device 84, such as a tablet computer, as illustrated in FIG. 12. The external controller 60 may comprise a separate unit or component and may be integrated in whole or in part with the user interface 62.

The external controller 62 may be electrically coupled with and may be adapted and configured to communicate with the controller 50 via wire leads 65 or wirelessly. Wireless communication may be by any suitable wireless arrangement including electromagnetically via RF transmission with suitable antennas, inductively via a suitable inductive coil arrangement, or by any other suitable wireless arrangement. Similarly, the external controller 60 also may be coupled to and adapted and configured to communicate with remote devices via telecommunications network 80 as illustrated in FIG. 12.

The external controller 60 can be adapted and configured to incorporate some or all of the functions and operability of the controller 50 described herein such that in some embodiments, an implantable controller 50 may not be present. Alternatively, the external controller 60 in combination with the user interface 62 may be adapted and configured to enable a user or operator to externally control some or all of the functions and operations of the controller 50, including for example the generation and control of the electrical noise stimulation signals, selection of electrodes 30 and application of the electrical noise stimulation signals to target tissue 12, and monitoring of sensor data generated by sensors S1, S2.

The external controller 60 also can be adapted and configured to control in whole or in part the use of an external power source 64, which is illustrated in FIG. 10 and described further below, to provide power remotely to the components within the implantable enclosure 16 illustrated in FIG. 11. The external controller 60 can be adapted and configured to control use of the external power source 64 to provide a source of power for the internal power source 52, for example if the internal power source comprises a transformer or voltage converter, and to provide power to recharge internal power source 52 if the internal power source 52 comprises rechargeable batteries. In embodiments without the internal power source 52, the external controller 60 can be adapted and configured to control use of the external power source 64 to directly provide power to the other components of the implantable enclosure 16, including the electrical signal generator 40 to generate the electrical noise stimulation signals. Further, in embodiments in which the electrical signal generator 40 is external to the patient 14, the external controller 60 can be adapted and configured to control use of the external power source 64 to directly provide power to the external electrical signal generator 40.

I. Power Sources.

An internal power source 52 may be enclosed within the implantable enclosure 16 and be implantable in a patient 14. The internal power source 52 may be electrically coupled to and provide operating power to the electrical signal generator 40, controller 50, and other components enclosed within the implantable enclosure 16, including the electrode interface 54, sensor interface 56, and communications interface 58 to the extent needed.

The internal power source 52 may comprise an internal source of power, such as a transformer, voltage converter, or the like that is fed by an external source of power, such as external power source 64 illustrated in FIG. 11 and described below. In that case, the internal power source 52 may be coupled to and receive power from the external source of power via a wired connection or wirelessly, for example via a suitable inductive coil arrangement.

Preferably, however, the internal power source 52 will comprise a self-contained source of power such as a suitable battery or batteries. Further, the battery or batteries preferably will be of the rechargeable type. Suitable batteries may include batteries of the lithium ion, lithium air, lithium/iodine, and lithium/manganese oxide types which are commercially available from numerous sources. The battery or batteries will preferably be rechargeable either via a wired connection to an external source of power, such as the external power source 64, or wirelessly, for example via a suitable inductive coil arrangement.

The external power source 64 is located external to the patient 14 and preferably is adapted to provide operating power for the external controller 60 and the user interface 62. The external power source 64 also is preferably adapted to function as a source of external power to the internal power source 52 as described above. In embodiments in which there is no internal power source 52, the external power source 64 also preferably will be adapted to provide power directly to the other components of the implantable enclosure 16, including the electrical signal generator 40 to generate the electrical noise stimulation signals. Further, in embodiments in which the electrical signal generator 40 is external to the patient 14, the external controller 60 will preferably be adapted to provide power directly to the external electrical signal generator 40. The external power source 64 may comprise any suitable source of power including but not limited to one or more connections to an external power grid, a generator, or one or more batteries.

J. Exemplary Telecommunications Networks.

With reference to FIG. 12, the example embodiments of the neuromodulation system 10 may be utilized upon or in connection with any telecommunications network 80 capable of transmitting data including voice data and other types of electronic data. For example, the controller 50 and the external controller 60 of the example embodiments of the neuromodulation system 10 may connect and communicate with remote devices using the telecommunications network 80. Examples of suitable telecommunications networks 80 for the example embodiments of the neuromodulation system 10 include but are not limited to global computer networks (e.g. Internet), wireless networks, cellular networks, satellite communications networks, cable communication networks (via a cable modem), microwave communications networks, peer-to-peer networks, local area networks (LAN), wide area networks (WAN), campus area networks (CAN), metropolitan-area networks (MAN), and home area networks (HAN). The communications interface 58 and the external controller 60 of the example embodiments of the neuromodulation system 10 may comprise the appropriate modems or other interfaces and may implement the appropriate protocols to enable the example embodiments of the neuromodulation system 10 to communicate with remote devices over the telecommunications network 80. The example embodiments of the neuromodulation system 10 may communicate via a single telecommunications network 80 or multiple telecommunications networks 80 concurrently. Various protocols may be utilized by the electronic devices for communications such as but not limited to HTTP, SMTP, FTP and WAP (Wireless Application Protocol). The example embodiments of the neuromodulation system 10 may be utilized in connection with various wireless networks such as but not limited to 3G, 4G, LTE, CDPD, CDMA, GSM, PDC, PHS, TDMA, FLEX, REFLEX, IDEN, TETRA, DECT, DATATAC, and MOBITEX. The example embodiments of the neuromodulation system 10 may also be utilized with online services and internet service providers.

The Internet is an exemplary telecommunications network for the example embodiments of the neuromodulation system 10 to operate upon or in connection with. The Internet is comprised of a global computer network having a plurality of computer systems around the world that are in communication with one another. Via the Internet, the computer systems are able to transmit various types of data between one another. The communications between the computer systems may be accomplished via various methods such as but not limited to wireless, Ethernet, cable, direct connection, telephone lines, and satellite.

K. Central Communication Unit.

The example embodiments of the neuromodulation system 10 may be in communication with a central communication unit 82. The central communication unit 82 may be comprised of any central communication site with which communications are preferably established. The central communication unit 82 may be comprised of a server computer, cloud based computer, virtual computer, personal computer or other computer system capable of receiving and transmitting data via IP networks and/or the telecommunication network. As can be appreciated, a modem or other communication device may be required between each of the central communication unit 82 and the corresponding telecommunications network 80. The central communication unit 82 may be comprised of any electronic system capable of receiving and transmitting information (e.g. voice data, computer data, etc.).

L. Mobile Device.

The example embodiments of the neuromodulation system 10 may be comprised of in part or may be in communication with a mobile device 84. For example, all or part of the external controller 60 illustrated in FIG. 10 and described above may be comprised of the mobile device 84. The mobile device 84 may be comprised of any type of computer for practicing the various aspects of the example embodiments of the neuromodulation system 10. For example, the mobile device 84 can be a personal computer (e.g. APPLE® based computer, an IBM based computer, or compatible thereof) or tablet computer (e.g. IPAD®). The mobile device 84 may also be comprised of various other electronic devices capable of sending and receiving electronic data including but not limited to smartphones, mobile phones, telephones, personal digital assistants (PDAs), mobile electronic devices, handheld wireless devices, two-way radios, smart phones, communicators, video viewing units, television units, television receivers, cable television receivers, pagers, communication devices, and digital satellite receiver units.

The mobile device 84 may be comprised of any conventional computer. A conventional computer preferably includes a display screen (or monitor), a printer, a hard disk drive, a network interface, and a keyboard. A conventional computer also includes a microprocessor, a memory bus, random access memory (RAM), read only memory (ROM), a peripheral bus, and a keyboard controller. The microprocessor is a general-purpose digital processor that controls the operation of the computer. The microprocessor can be a single-chip processor or implemented with multiple components. Using instructions retrieved from memory, the microprocessor controls the reception and manipulations of input data and the output and display of data on output devices. The memory bus is utilized by the microprocessor to access the RAM and the ROM. RAM is used by microprocessor as a general storage area and as scratch-pad memory, and can also be used to store input data and processed data. ROM can be used to store instructions or program code followed by microprocessor as well as other data. A peripheral bus is used to access the input, output and storage devices used by the computer. These devices may include a display screen, a printer device, a hard disk drive, and/or a network interface. The display screen comprises an output device that displays images of data provided by the microprocessor via the peripheral bus or provided by other components in the computer. A keyboard controller is used to receive input from the keyboard and send decoded symbols for each pressed key to microprocessor over bus. The keyboard is used by a user to input commands and other instructions to the computer system. Other types of user input devices can also be used in conjunction with the example embodiments of the neuromodulation system 10. For example, pointing devices such as a computer mouse, a track ball, a stylus, or a tablet to manipulate a pointer on a screen of the computer system. All or part of the user interface 62 of the example embodiments of the neuromodulation system 10 illustrated in FIG. 10 and described above can be comprised in whole or in part by the display screen, keyboard, and/or other input devices described above. The printer device when operating as a printer provides an image on a sheet of paper or a similar surface. The hard disk drive can be utilized to store various types of data. The microprocessor together with an operating system operate to execute computer code and produce and use data. The computer code and data may reside on RAM, ROM, or hard disk drive. The computer code and data can also reside on a removable program medium and loaded or installed onto computer system when needed. Removable program mediums include, for example, CD-ROM, PC-CARD, USB drives, floppy disk and magnetic tape. The network interface circuit is utilized to send and receive data over a network connected to other computer systems. An interface card or similar device and appropriate software implemented by microprocessor can be utilized to connect the computer system to an existing network and transfer data according to standard protocols.

M. Operation of Preferred Embodiment.

In an example of use of an example embodiment of the neuromodulation system 10, one or more leads 18 with electrodes 30 may be inserted in a patient 14 in conventional fashion and positioned in desired positions in, on, and around the target tissue 12 to receive treatment as described herein. Similarly, sensors S1, S2 are implanted in the patient 14 in, on, or around the target tissue 12 either coincident with or in proximity to the electrodes 30. One or more leads 18 extending from the electrodes 30 and the sensors S1, S2 can be connected to an electrical signal generator 40, controller 50, external controller 60, and/or external user interface 62. Typically, but not necessarily, the electrical signal generator 40 will be external to the patient 14 while the example embodiment of the neuromodulation system 10 is being set up for permanent implantation in the patient 14 or if the system is being set up to provide only temporary treatment. Once the setup is completed, the implantable electrical signal generator 40 typically will be permanently implanted in the patient 14 in the implantable enclosure 16.

A user or operator may use the user interface 62 and the controller 50 or external controller 60 to select an electrode 30 or combination of electrodes 30, cause the electrical signal generator 40 to selectively generate and deliver electrical noise stimulation signals to the target tissue 12, and monitor the sensor data produced by the sensors S1, S2 as described herein. The controller 50 or external controller 60 controls the electrical signal generator 40 as described herein to scan or sweep the center frequency of a relatively narrow band of electrical noise stimulation signals across the entire bandwidth or a portion of the bandwidth of possible frequencies for such signals and determines a plurality of peak values of impedance present at a plurality of different center frequencies. The process is repeated for a plurality of different selected electrodes 30 and/or combinations of electrodes 30 as desired.

If necessary or desired, one or more of the electrodes 30 and sensors S1, S2 can be repositioned, for example to provide better contact, alter the distance and/or orientation of the electrodes 30 and/or sensors S1, S2 relative to the target tissue 12, better position the electrodes 30 in specific neural and/or non-neural tissue of the target tissue 12 etc. in order to achieve better peak values of the impedance. The process to determine the peak values of impedance in relation to frequency can then be repeated. One or more of the electrodes 30 and sensors S1, S2 can be repositioned and the process to determine the peak values of impedance can be repeated as many times as necessary in order to obtain one or more sets or pluralities of peak values of impedance that are satisfactory for use in providing treatment.

The user or operator then uses the user interface 62 and the controller 50 or external controller 60 to generate and deliver electrical noise stimulation signals to the target tissue 12 of the patient 14 to stimulate or modulate the target tissue 12 and provide treatment for one or more conditions, including one or more of the conditions identified herein. The electrical noise stimulation signals are generated and delivered to the target tissue 12 in the manner described herein to optimize and maximize the electric field in the target tissue 12 by maximizing the voltage while maintaining an acceptably low level of current density to provide an optimal therapeutic result while also preventing overheating and damage to the target tissue 12 and discomfort to the patient 14.

Once the desired therapeutic results are achieved, the leads 18 can be connected to the lead connection ports 19 of the implantable enclosure 16 to electrically couple the electrodes 30 and sensors S1, S2 to the implantable controller 50 and the implantable electrical signal generator 40 within the implantable enclosure 16. The implantable enclosure 16 is then implanted in the patient permanently in conventional fashion.

Thereafter, the patient 14 or a user or operator of the example embodiment of the neuromodulation system 10 can use the external controller 60 if included or another remote device to periodically communicate with the implantable controller 50 and manually initiate a treatment dose when needed. The treatment dose can have a preset duration and/or preset parameters for the electrical noise stimulation signals, such as peak voltage level. Alternatively, the duration and some or all parameters of the electrical noise stimulation signals can be manually selected by the patient 14 or a user or operator. Also alternatively, the implantable controller 50 can be configured to automatically initiate treatment doses on a predetermined schedule and with predetermined duration and preset parameters of the electrical noise stimulation signals.

Any and all headings are for convenience only and have no limiting effect. Unless otherwise defined, all technical and scientific terms used herein have the same meaning as commonly understood by one of ordinary skill in the art to which this invention belongs. Although specific terms are employed herein, they are used in a generic and descriptive sense only and not for purposes of limitation. All publications, patent applications, patents, and other references mentioned herein are incorporated by reference in their entirety to the extent allowed by applicable law and regulations.

Any data structures and code described in this detailed description are typically stored on a computer readable storage medium, which may be any device or medium that can store code and/or data for use by a computer system. This includes, but is not limited to, magnetic and optical storage devices such as disk drives, magnetic tape, CDs (compact discs), DVDs (digital video discs), and computer instruction signals embodied in a transmission medium (with or without a carrier wave upon which the signals are modulated). For example, the transmission medium may include a telecommunications network, such as the Internet.

At least one embodiment of the neuromodulation system and method with feedback optimized electrical field generation is described above with reference to block and/or flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention. These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer-readable program code or program instructions embodied therein, the computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks. Accordingly, blocks of the block diagrams and/or flow diagrams support combinations of means for performing the specified functions, combinations of elements or steps for performing the specified functions, and program instruction means for performing the specified functions. It will also be understood that each block of the block diagrams and/or flow diagrams, and combinations of blocks in the block diagrams and/or flow diagrams, can be implemented by special-purpose, hardware-based computer systems that perform the specified functions, elements or steps, or combinations of special-purpose hardware and computer instructions.

The present invention may be embodied in other specific forms without departing from the spirit or essential attributes thereof, and it is therefore desired that the present embodiment be considered in all respects as illustrative and not restrictive. Many modifications and other embodiments of the neuromodulation system and method with feedback optimized electrical field generation will come to mind to one skilled in the art to which this invention pertains and having the benefit of the teachings presented in the foregoing description and the associated drawings. Further, features illustrated or described as part of one embodiment may be used on another embodiment to yield a still further embodiment. Therefore, it is to be understood that the invention is not to be limited to the specific embodiments disclosed and that modifications and other embodiments are intended to be included within the scope of the appended claims. Although methods and materials similar to or equivalent to those described herein can be used in the practice or testing of the neuromodulation system and method with feedback optimized electrical field generation, suitable methods and materials are described above. Thus, the neuromodulation system and method with feedback optimized electrical field generation is not intended to be limited to the embodiments shown, but is to be accorded the widest scope consistent with the principles and features disclosed herein.

What is claimed is:

1. A method of providing therapy to a patient, comprising:
generating an electrical noise stimulation signal from an electrical signal generator;
receiving the electrical noise stimulation signal by an electrode;
applying an electric field in a target tissue of the patient by the electrode in response to the electrical noise stimulation signal, wherein the target tissue comprises a neural tissue, a non-neural tissue, or a combination thereof;
receiving a value of a physical parameter associated with the target tissue in response to application of the electric field in the target tissue; and
automatically optimizing the electric field in response to the value of the physical parameter to produce a therapeutic effect within the target tissue without the value of the physical parameter indicating potential damage to the target tissue by the electrical noise stimulation signal.

2. The method of claim 1, including the step of measuring the value of the physical parameter by a sensor.

3. The method of claim 2, wherein the sensor comprises a temperature sensor and the physical parameter of the target tissue comprises a temperature.

4. The method of claim 2, wherein the sensor comprises an impedance sensor and the physical parameter of the target tissue comprises an impedance.

5. The method of claim 1, wherein the step of automatically optimizing the electric field comprises adjusting the electrical noise stimulation signal from the electrical signal generator.

6. The method of claim 1, wherein the step of automatically optimizing the electric field comprises reducing a current density or a current flow to the target tissue if the value of the physical parameter indicates potential damage to the target tissue.

7. The method of claim 1, wherein the step of automatically optimizing the electric field comprises reducing a strength of the electric field if the value of the physical parameter indicates potential damage to the target tissue.

8. The method of claim 1, wherein the step of automatically optimizing the electric field comprises limiting a dose of the electric field if the value of the physical parameter indicates potential damage to the target tissue.

9. The method of claim 1, wherein the step of automatically optimizing the electric field comprises controlling the electric field to maximize a voltage of the electric field.

10. The method of claim 1, wherein the value of the physical parameter that is associated with potential damage to the target tissue comprises a predetermined impedance.

11. The method of claim 1, wherein the value of the physical parameter that is associated with potential damage to the target tissue comprises a predetermined temperature.

12. The method of claim 1, including the step of receiving input about sensations of the patient in response to application of the electric field to the target tissue.

13. A method of providing therapy to a patient, comprising:
implanting an electrode into or near a target tissue of the patient, wherein the electrode is adapted to receive an electrical noise stimulation signal from an electrical signal generator and to produce an electric field for application to the target tissue of the patient, and wherein the target tissue comprises a neural tissue, a non-neural tissue, or a combination thereof;
implanting a sensor into or near the target tissue of the patient, wherein the sensor is configured to generate a sensor data indicative of a value of a physical parameter associated with the target tissue in response to application of the electrical noise stimulation signal;
transmitting the electrical noise stimulation signal from the electrical signal generator to the electrode;
applying the electric field from the electrode to the target tissue;
generating the sensor data by the sensor;
receiving the sensor data by a controller; and
automatically controlling the electrical signal generator by the controller in response to the sensor data to generate the electrical noise stimulation signal to optimize the electric field to produce a therapeutic effect within the target tissue without the value indicating potential damage to the target tissue by the electrical noise stimulation signal.

14. The method of claim 13, wherein the sensor comprises a temperature sensor and the physical parameter of the target tissue comprises a temperature.

15. The method of claim 13, wherein the sensor comprises an impedance sensor and the physical parameter of the target tissue comprises an impedance.

16. The method of claim 13, wherein the step of automatically controlling the electrical signal generator comprises reducing a strength of the electric field if the value of the physical parameter indicates potential damage to the target tissue.

17. The method of claim 13, wherein the step of automatically controlling the electrical signal generator comprises reducing a current density or a current flow to the target tissue if the value of the physical parameter indicates potential damage to the target tissue.

18. The method of claim 13, wherein the step of automatically controlling the electrical signal generator comprises limiting a dose of the electric field if the value of the physical parameter indicates potential damage to the target tissue.

19. The method of claim 13, wherein the step of automatically controlling the electrical signal generator comprises controlling the electric field to maximize a voltage of the electric field.

20. The method of claim 13, wherein the value of the physical parameter that is associated with potential damage to the target tissue comprises a predetermined impedance.

21. The method of claim 13, wherein the value of the physical parameter that is associated with potential damage to the target tissue comprises a predetermined temperature.

22. The method of claim 13, including the step of receiving input about sensations of the patient in response to application of the electric field to the target tissue.

23. A method of providing therapy to a patient, comprising:
  generating an electrical noise stimulation signal;
  applying the electrical noise stimulation signal to produce an electric field in a target tissue of the patient, wherein the target tissue comprises a neural tissue, a non-neural tissue, or a combination thereof;
  sensing a value of a physical parameter associated with the target tissue in response to application of the electrical noise stimulation signal; and
  automatically optimizing the electric field in response to the value of the physical parameter to produce a therapeutic effect within the target tissue without the value of the physical parameter indicating potential damage to the target tissue by the electrical noise stimulation signal.

24. The method of claim 23, including the step of measuring the value of the physical parameter by a temperature sensor, wherein the physical parameter of the target tissue comprises a temperature.

25. The method of claim 23, including the step of measuring the value of the physical parameter by an impedance sensor, wherein the physical parameter of the target tissue comprises an impedance.

26. The method of claim 23, wherein the step of automatically optimizing the electric field comprises adjusting the electrical noise stimulation signal from an electrical signal generator.

27. The method of claim 23, wherein the step of automatically optimizing the electric field comprises reducing a strength of the electric field if the value of the physical parameter indicates potential damage to the target tissue.

28. The method of claim 23, wherein the step of automatically optimizing the electric field comprises reducing a current density or a current flow to the target tissue if the value of the physical parameter indicates potential damage to the target tissue.

29. The method of claim 23, wherein the step of automatically optimizing the electric field comprises limiting a dose of the electric field if the value of the physical parameter indicates potential damage to the target tissue.

30. The method of claim 23, wherein the step of automatically optimizing the electric field comprises controlling the electric field to maximize a voltage of the electric field.

* * * * *